United States Patent
Wlodecki et al.

(10) Patent No.: US 6,894,062 B1
(45) Date of Patent: May 17, 2005

(54) QUINOLINE DERIVATIVES

(75) Inventors: Bishop Wlodecki, Preston, CT (US); Gene M. Bright, Groton, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 10/664,706

(22) Filed: Sep. 18, 2003

Related U.S. Application Data

(60) Provisional application No. 60/425,518, filed on Nov. 12, 2002.

(51) Int. Cl.$^7$ ...................... C07D 401/02; A61K 31/47
(52) U.S. Cl. ..................................... 514/314; 546/167
(58) Field of Search .......................... 546/167; 514/314

(56) References Cited

FOREIGN PATENT DOCUMENTS

| EP | 0173585 | 3/1985 |
|---|---|---|
| NL | 812911 | 9/1951 |

OTHER PUBLICATIONS

Diaz de Arce, Humberto; "Some Derivatives of 8–Bromo–6–methylquinoline", J. American Chemical Society, vol. 72, 1950, pp. 2971–2974; XP002273437.

Manabe, Kel; "Receptors for Oxo Acids: Effects of Intra–Ion Pair Hydrogen Bonding on Acid–Base Equilibria", J. Org. Chem., vol. 58, 1993, pp. 6692–6700 XP–002273436.

Steck, Edgar A.; "Quinolines. III. The Synthesis of 5– and 7–Chloro– and Bromo–3–methyl–4–dialkylaminoalkyl-aminoquinolines", J. American Chemical Society, vol. 68, 1946, pp. 380–383, XP–002273436.

Alabaster, C. T., 2(1H)–Quinolinones with Cardiac Stimulant Activity. 1. Synthesis and Biological Activities of (Six–Membered Heteroaryl)–Substituted Derivatives. J. Med. Chem., vol. 31, 1988, pp. 2048–2056, XP–002273434.

Davis, Steven E., 2,4–Diamino–5–benzylpyrimidines and Analogues as Antibacterial Agents. 11.Quinolylmethyl Analogues with Basic Substituents Conveying Specificity, J. Med. Chem, vol. 32, 1989, pp. 1936–1942, XP–002273433.

Jacobs, Christopher, "1–Imidazolyl(alkyl)–Substituted Di–and Tetrahydroquinolines and Analogues Syntheses and Evaluation of Dual Inhibitors of Thromboxane A2 Synthase and Aromatase" J. Med. Chem. vol. 43, 2000, pp. 1841–1851, XP–002273432.

*Primary Examiner*—Zinna Northington Davis
(74) *Attorney, Agent, or Firm*—Peter C. Richardson; Lorraine B. Ling; Jolene W. Appleman

(57) ABSTRACT

The present invention relates to compounds of Formula I,

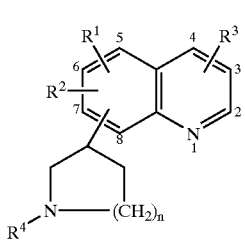

wherein $R^1$, $R^2$, $R^3$, $R^4$, and n are as defined, and to pharmaceutically acceptable salts of said compounds. Compounds of Formula I have activity in agonizing 5HT7 receptors and are useful in treating, for example, disorders that can be treated by modulating circadian rhythms.

10 Claims, No Drawings

QUINOLINE DERIVATIVES

CROSS-REFERENCE TO RELATED APPLICATIONS

This application claims priority from U.S. Provisional Application Ser. No. 60/425,518, filed Nov. 12, 2002.

BACKGROUND OF THE INVENTION

The present invention relates to novel quinoline derivatives, to intermediates used in their preparation, to pharmaceutical compositions containing them and to their medicinal use. The compounds of the present invention are agonists of serotonin 7 (5HT7) receptors. They are useful in treating CNS disorders, including depression and disorders that can be treated by modulating circadian rhythms. Examples of such disorders and conditions are seasonal affective disorder, bipolar disorder, jet lag, sleep disorders such as circadian sleep rhythm disorder, sleep deprivation, REM sleep disorders, hypersomnia, parasomnias, sleep-wake cycle disorders, narcolepsy, sleep disorders associated with blindness, sleep disorders associated with obesity, and sleep disorders associated with shift work or irregular work schedules; nocturnal enuresis, and restless leg syndrome.

Serotonin 7 receptors are present in the suprachiasmatic nucleus (SCN), the brain region that contains the biological clocks, and their activation leads to a resetting of the clocks as a function of dose and timing of treatment. Such a mechanistic link is evident in numerous paradigms—in in vitro electrophysiological studies of SCN neuronal activity, and in light induced changes in wheel running behavior and nighttime melatonin suppression—in each case activation of 5HT7 receptors having the potential to modulate both clock function and the clock resetting ability of light. Full agonists and partial agonists of the 5HT7 receptor therefore offer a wide range of clinically useful therapeutics.

Glennon's article "Serotonin Receptors: Clinical Implications", *Neuroscience and Behavioral Reviews*, 14, 35–47 (1990), refers to the pharmacological effects associated with serotonin receptors including appetite suppression, thermoregulation, cardiovascular/hypotensive effects, sleep, psychosis, anxiety, depression, nausea, emesis, Alzheimer's disease, Parkinson's disease and Huntington's disease.

SUMMARY OF THE INVENTION

The present invention relates to compounds of the Formula

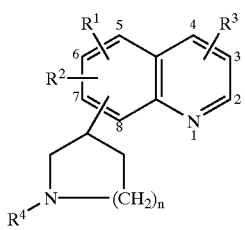

I wherein $R^1$, $R^2$ and $R^3$ are independently selected from hydrogen, halo, ($C_1$–$C_6$)alkyl optionally substituted with from one to three halo (i.e., chloro, fluoro, bromo or iodo) atoms; and ($C_1$–$C_6$)alkoxy optionally substituted with from one to three halo atoms;

$R^4$ is hydrogen or ($C_1$–$C_3$) alkyl; and n is one or two;

and to the pharmaceutically acceptable salts thereof.

Compounds of Formula I and their pharmaceutically acceptable salts (also referred to collectively herein as "the active compounds of this invention") are potent agonists of 5HT7 receptors.

As used herein, the non-quinoline ring refers to the ring containing the nitrogen to which $R^4$ is attached, i.e.,

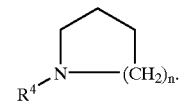

In one embodiment, the present invention provides compounds of Formula I wherein n is 1. In another embodiment, the present invention provides compounds of Formula I wherein either $R^1$ and $R^2$ are both hydrogen or one of $R^1$ and $R^2$ is hydrogen and the other is attached at position 5. In another embodiment, n is 1, and either $R^1$ and $R^2$ are both hydrogen or one of $R^1$ and $R^2$ is hydrogen and the other is attached at position 5.

In another embodiment, the invention provides compounds of Formula I wherein the non-quinoline ring is attached at position 7 or 8.

In another embodiment, compounds of Formula I are provided wherein n is 1, and either $R^1$ and $R^2$ are both hydrogen or one of $R^1$ and $R^2$ is hydrogen and the other is attached at position 5, and the non-quinoline ring is attached at position 7.

In another embodiment, the present provides compounds of Formula I having the Formula:

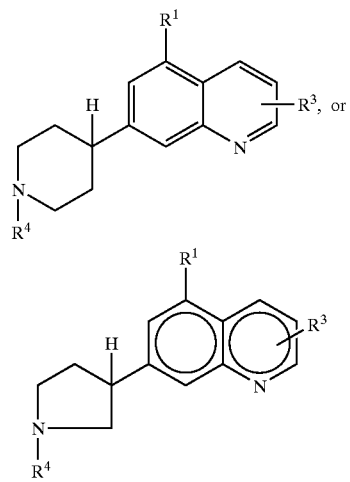

wherein $R^4$, $R^1$ and $R^3$ are defined as above.

Examples of preferred compounds of the Formula I of the invention are:
R and S-(3-Ethyl-7-methyl-8-piperidin-3-yl-quinoline);
R, S-(3-Ethyl-7-methyl-8-piperidin-3-yl-quinoline);
R and S-(3,6-Dimethyl-8-piperidin-3-yl-quinoline);
R, S-(3,6-Dimethyl-8-piperidin-3-yl-quinoline);
R and S-(3,7-Dimethyl-8-piperidin-3-yl-quinoline);
R, S-(3,7-Dimethyl-8-piperidin-3-yl-quinoline);
R and S-(3,5-Dimethyl-8-piperidin-3-yl-quinoline);
R and S-(3,5-Dimethyl-8-piperidin-3-yl-quinoline);
R and S-(6-Chloro-3-methyl-8-piperidin-3-yl-quinoline);
R, S-(6-Chloro-3-methyl-8-piperidin-3-yl-quinoline);
R and S-(3-Ethyl-8-piperidin-3-yl-quinoline);
R, S-(3-Ethyl-8-piperidin-3-yl-quinoline);
R and S-(4-Methyl-8-piperidin-3-yl-quinoline);
R, S-(4-Methyl-8-piperidin-3-yl-quinoline);

R and S-(3-Methyl-8-piperidin-3-yl-quinoline);
R, S-(3-Methyl-8-piperidin-3-yl-quinoline);
R and S-(3-Ethyl-8-piperidin-3-yl-quinoline);
R, S-(3-Ethyl-8-piperidin-3-yl-quinoline);
R and S-(Ethyl-7-piperidin-3-yl-quinoline);
R, S-(Ethyl-7-piperidin-3-yl-quinoline);
R and S-[3-Methyl-8-(1-methyl-piperidin-3-yl)quinoline]; and
R, S-[3-Methyl-8-(1-methyl-piperidin-3-yl)-quinoline];
and pharmaceutically acceptable salts thereof.

Other examples of specific compounds of the Formula I of the invention are:
3-Ethyl-7-methyl-8-(1-methyl-piperidin-3-yl)-quinoline;
3-Ethyl-8-methyl-8-(1-ethyl-piperidin-3-yl)-7-methyl-quinoline;
3,6-Dimethyl-8-(1-methyl-piperidin-3-yl)quinoline;
8-(1-Ethyl-piperidin-3-yl)-3,6-dimethyl-quinoline;
3,7-Dimethyl-8-(1-methyl-piperidin-3-yl)-quinoline;
8-(1-Ethyl-piperidin-3-yl)-3,7-dimethyl-quinoline;
3,5-Dimethyl-8-(1-methyl-piperidin-3-yl)-quinoline;
8-(1-Ethyl-7-piperidin-3-yl)-3,5-dimethyl-quinoline;
6-Chloro-3-methyl-8-(1-methyl-piperidin-3-yl)-quinoline;
6-Chloro-8-(1-ethyl-piperidin-3-yl)-3-methyl-quinoline;
3-Ethyl-8-(1-methyl-piperidin-3-yl)-quinoline;
3-Ethyl-8-(1-ethyl-piperidin-3-yl)-quinoline;
4-Methyl-8-(1-methyl-piperidin-3-yl)-quinoline;
8-(1-Ethyl-piperidin-3-yl)-4-methyl-quinoline;
3-Methyl-8-(1-methyl-piperidin-3-yl)-quinoline;
8-(1-Ethyl-piperidin-3-yl)-3-methyl-quinoline;
3-Ethyl-8-(1-methyl-pyrrolidin-3-yl)-quinoline;
3-Ethyl-8-(1-ethyl-pyrrolidin-3-yl)-quinoline;
3-Ethyl-7-(1-methyl-piperidin-3-yl)-quinoline;
3-Ethyl-7-(1-ethyl-piperidin-3-yl)-quinoline;
3-Ethyl-7-pyrrolidin-3-yl)-quinoline;
3-Ethyl-7-(1-methyl-pyrrolidin-3-yl)-quinoline; and
3-Ethyl-7-(1-ethyl-pyrrolidin-3-yl)-quinoline;
and pharmaceutically acceptable salts thereof.

The present invention also provides a pharmaceutical composition comprising a therapeutically effective amount of a compound of Formula I, or a pharmaceutically acceptable salt thereof, and a pharmaceutically acceptable carrier.

The present invention also provides a method for treating a disorder or condition that can be treated by modulating serotonergic neurotransmission in a mammal, comprising administering to a mammal requiring such treatment a serotonin 7 receptor agonizing effective amount of a compound of Formula I or a pharmaceutically acceptable salt thereof.

The present invention also provides a pharmaceutical composition for treating a condition or disorder that can be treated by modulating serotonergic neurotransmission in a mammal, comprising:
  a) a pharmaceutically acceptable carrier;
  b) an amount of a first compound of Formula I or a pharmaceutically acceptable salt thereof; and
  c) an amount of a second compound selected from the group consisting of a 5HT reuptake inhibitor, a 5HT7 receptor antagonist or a NK1 receptor antagonist or a pharmaceutically acceptable salt thereof;
wherein the amounts of (b) and (c) are together effective in treating such disorder or condition.

The present invention also provides a method for treating a disorder or condition that can be treated by modulating serotonergic neurotransmission in a mammal, comprising administering to a mammal requiring such treatment:
  a) an amount of a compound of Formula I or a pharmaceutically acceptable salt thereof; and
  b) an amount of a second compound selected from the group consisting of 5HT reuptake inhibitor, a 5HT7 receptor antagonist and an NK1 receptor antagonist or pharmaceutically acceptable salt thereof;
wherein the amounts of (a) and (b) are together effective in treating such disorder or condition.

The present invention also provides a method for treating a disorder or condition selected from depression, anxiety, avoidant personality disorder, premature ejaculation, eating disorders, migraine, premenstrual syndrome, premenstrual dysphoric disorder, seasonal affective disorder, bipolar disorder, jet lag, sleep disorder, nocturnal enuresis, and restless leg syndrome in a mammal, comprising administering to a mammal in need of such treatment an amount of a compound of Formula I, or a pharmaceutically acceptable salt thereof, which amount is (a) effective in treating such disorder or condition, or (b) effective in agonizing 5HT7 receptors.

In different embodiments of the methods described in the preceding paragraphs, the sleep disorder is circadian sleep rhythm disorder, sleep deprivation, REM sleep disorder, hypersomnia, parasomnia, sleep-wake cycle disorder, sleep disorder associated with blindness, sleep disorder associated with obesity, narcolepsy or sleep disorder associated with shift work or irregular work schedules.

The present invention also provides a method of treating a disorder or condition selected from depression, anxiety, avoidant personality disorder, premature ejaculation, eating disorders, migraine, premenstrual syndrome, premenstrual dysphoric disorder, seasonal affective disorder, bipolar disorder, jet lag, sleep disorder, nocturnal enuresis, and restless leg syndrome in a mammal, comprising administering to a mammal requiring such treatment: (a) and amount of a first compound of Formula I or pharmaceutically acceptable salt thereof; and (b) an amount of a second compound selected from the group consisting of a 5HT7 receptor antagonist, a NK1 receptor antagonist and an a 5HT7 receptor antagonist or pharmaceutically acceptable salts of said second compound; wherein the amounts of (a) and (b) are together effective in treating such disorder or condition.

In different embodiments of the method described in the preceding paragraph, the sleep disorder is circadian sleep rhythm disorder, sleep deprivation, REM sleep disorder, hypersomnia, parasomnia, sleep-wake cycle disorders, sleep disorder associated with blindness, sleep disorder associated with obesity, narcolepsy, or sleep disorder associated with shift work or irregular work schedules.

The present invention also provides compounds of the Formula

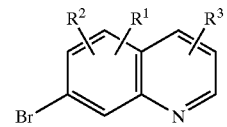

XII and compounds of the Formula

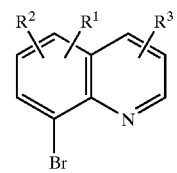

wherein for each of the above two Formulae $R^1$, $R^2$ and $R^3$ are independently selected from hydrogen, halo, ($C_1$–$C_6$)

alkyl optionally substituted with from one to three halo atoms; and ($C_1$–$C_6$)alkoxy optionally substituted with from one to three halo atoms. Compounds of these two Formulae are useful as intermediates for synthesizing compounds of Formula I.

The present invention also provides a method for synthesizing a compound of the Formula

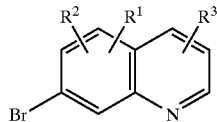

XII wherein $R^1$, $R^2$ and $R^3$ are independently selected from hydrogen, halo, ($C_1$–$C_6$)alkyl optionally substituted with from one to three halo atoms; and ($C_1$–$C_6$)alkoxy optionally substituted with from one to three halo atoms;

which method comprises reacting a compound of the Formula

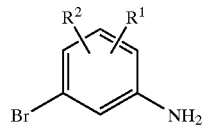

X wherein $R^1$ and $R^2$ are as recited above,
with a compound of the Formula

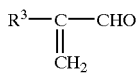

XI wherein $R^3$ is as recited above,
or with a compound

$R^3$—OH wherein $R^3$ is as recited above,
wherein said reaction is in the presence of an aqueous acid and 3-nitrobenzenesulfonic acid or a salt thereof, and wherein said reaction is at a temperature of from about 100° C. to about 140° C.

The present invention also provides a method for synthesizing a compound of the Formula

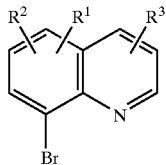

wherein $R^1$, $R^2$ and $R^3$ are independently selected from hydrogen, halo, ($C_1$–$C_6$)alkyl optionally substituted with from one to three halo atoms; and ($C_1$–$C_6$)alkoxy optionally substituted with from one to three halo atoms;

which method comprises reacting a compound of the Formula

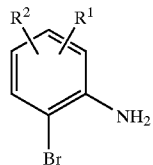

wherein $R^1$ and $R^2$ are as recited above, with a compound of the Formula

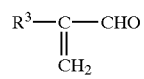

XI wherein $R^3$ is as recited above,
or, preferably, with a compound

$R^3$—OH wherein $R^3$ is as recited above,
wherein said reaction is in the presence of an aqueous acid and 3-nitrobenzenesulfonic acid or a salt thereof, and wherein said reaction is at a temperature of from about 100° C. to about 140° C.

In either of the above-described synthetic methods, the aqueous acid is in one embodiment sulfuric acid.

Compounds of Formula I may contain chiral centers and therefore may exist in different enantiomeric and diastereomeric forms. This invention relates to all optical isomers and all stereoisomers of compounds of the Formula I, both as racemic mixtures and as individual enantiomers and diastereoisomers of such compounds, and mixtures thereof, and to all pharmaceutical compositions and methods of treatment defined above that contain or employ them, respectively. Individual isomers can be obtained by known methods, such as optical resolution, optically selective reaction, or chromatographic separation in the preparation of the final product or its intermediate. Individual enantiomers of the compounds of Formula I may have advantages, as compared with the racemic mixtures of these compounds, in the treatment of various disorders or conditions.

Insofar as the compounds of Formula I of this invention are basic compounds, they are capable of forming a wide variety of different salts with various inorganic and organic acids which are used to prepare the pharmaceutically acceptable acid addition salts of the aforementioned base compounds of this invention are those which form non-toxic acid addition salts, i.e., salts containing pharmaceutically acceptable anions, such as the hydrochloride, hydrobromide, hydroiodide, nitrate, sulfate or bisulfate, phosphate or acid phosphate, acetate, lactate, curate or acid citrate, tartrate or bi-tartrate, succinate, maleate, fumarate, gluconate, saccharate, benzoate, methanesulfonate, ethanesulfonate, benzenesulfonate, p-toluenesulfonate and pamoate (i.e., 1,1'-methylenebis-(2-hydroxy-3-naphthoate))salts.

The present invention also includes isotopically labelled compounds, which are identical to those recited in Formula I, but for the fact that one or more atoms are replaced by an atom having an atomic mass or mass number different from the atomic mass or mass number usually found in nature. Examples of isotopes that can be incorporated into compounds of the present invention include isotopes of hydrogen, carbon, nitrogen, oxygen, phosphorous, sulfur, fluorine and chlorine, such as $^2H$, $^3H$, $^{13}C$, $^{11}C$, $^{14}C$, $^{15}N$, $^{18}O$, $^{17}O$, $^{31}P$, $^{32}P$, $^{35}S$, $^{18}F$, and $^{36}Cl$, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically labelled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labelled compounds of Formula I of this invention and prodrugs thereof can generally be prepared by carrying out the procedures disclosed in the Schemes and/or in the Examples below, by substituting a readily available isotopically labelled reagent for a non-isotopically labelled reagent.

"Serotonin" and "5HT7" are used interchangeably herein, unless otherwise indicated. "Serotonin 7 agonists are useful for the treatment of depression.

As used herein, the term "depression" includes major depressive disorder; single episode or recurrent major depressive episodes; recurrent depression; dysthymia; cyclothymia; depressive disorders not otherwise specified; seasonal affective disorder; and bipolar disorders, for example, bipolar I disorder, bipolar II disorder and bipolar disorder not otherwise specified.

Other mood disorders encompassed within the term "depression", as used herein, include dysthymic disorder with early or late onset and with or without atypical features; dementia of the Alzheimer's type, with early or late onset, with depressed mood; vascular dementia with depressed mood; mood disorders induced by alcohol, amphetamines, cocaine, hallucinogens, inhalants, opioids, phencyclidine, sedatives, hypnotics, anxiolytics or other substances; schizoaffective disorder of the depressed type; and adjustment disorder with depressed mood.

Encompassed within the term "depression", as used herein, are: depression in cancer patients, depression in Parkinson's patients, postmyocardial infarction depression, subsyndromal symptomatic depression, depression in infertile women, pediatric depression, child abuse induced depression, and post partum depression.

Major depression is characterized by feelings of intense sadness and despair, mental slowing and loss of concentration, pessimistic worry, agitation, and self-deprecation. Physical changes also occur, especially in severe or "melancholic" depression. These include insomnia or hypersomnia, anorexia and weight loss (or sometimes overeating), decreased energy and libido, and disruption of normal circadian rhythms of activity, body temperature, and many endocrine functions.

The Serotonin 7 agonists of Formula I of the invention are also useful for the treatment of anxiety. As used herein, the term "anxiety" includes anxiety disorders, such as panic disorder with or without agoraphobia, agoraphobia without history of panic disorder, specific phobias, for example, specific animal phobias, social phobias, obsessive-compulsive disorder, stress disorders including post-traumatic stress disorder and acute stress disorder, and generalized anxiety disorders.

"Generalized anxiety" is typically defined as an extended period (e.g., at least six months) of excessive anxiety or worry with symptoms on most days of that period. The anxiety and worry is difficult to control and may be accompanied by restlessness, being easily fatigued, difficulty concentrating, irritability, muscle tension, and disturbed sleep.

"Panic disorder" is defined as the presence of recurrent panic attacks followed by at least one month of persistent concern about having another panic attack. A "panic attack" is a discrete period in which there is a sudden onset of intense apprehension, fearfulness or terror. During a panic attack, the individual may experience a variety of symptoms including palpitations, sweating, trembling, shortness of breath, chest pain, nausea and dizziness. Panic disorder may occur with or without agoraphobia.

"Phobias" includes agoraphobia, specific phobias and social phobias. "Agoraphobia" is characterized by an anxiety about being in places or situations from which escape might be difficult or embarrassing or in which help may not be available in the event of a panic attack. Agoraphobia may occur without history of a panic attack. A "specific phobia" is characterized by clinically significant anxiety provoked by a feared object or situation. Specific phobias include the following subtypes: animal type, cued by animals or insects; natural environment type, cued by objects in the natural environment, for example storms, heights or water; blood-injection-injury type, cued by the sight of blood or an injury or by seeing or receiving an injection or other invasive medical procedure; situational type, cued by a specific situation such as public transportation, tunnels, bridges, elevators, flying, driving or enclosed spaces; and other type, where fear is cued by other stimuli. Specific phobias may also be referred to as simple phobias. A "social phobia" is characterized by clinically significant anxiety provoked by exposure to certain types of social or performance circumstances. Social phobia may also be referred to as social anxiety disorder.

Other anxiety disorders encompassed within the term "anxiety" include anxiety disorders induced by alcohol, amphetamines, caffeine, cannabis, cocaine, hallucinogens, inhalants, phencyclidine, sedatives, hypnotics, anxiolytics and other substances, and adjustment disorders with anxiety or with mixed anxiety and depression.

Anxiety may be present with or without other disorders, such as depression in mixed anxiety and depressive disorders. The compositions of the present invention are therefore useful in the treatment of anxiety with or without accompanying depression.

The term "alkyl", as used herein, unless otherwise indicated, includes saturated monovalent hydrocarbon radicals having straight, branched or cyclic moieties or combinations thereof. Examples of "alkyl" groups include, but are not limited to, methyl, ethyl, propyl, isopropyl, butyl, iso- sec- and tert-butyl, pentyl, hexyl, heptyl, 3-ethylbutyl, cyclopropyl, cyclobutyl, cyclopentyl, cyclohexyl, cycloheptyl, norbornyl, and the like.

The term "alkoxy", as used herein, unless otherwise indicated, means "alkyl-O-", wherein "alkyl" is as defined above. Examples of "alkoxy" groups include, but are not limited to, methoxy, ethoxy, propoxy, butoxy and pentoxy.

The term "alkenyl", as used herein, unless otherwise indicated, includes unsaturated hydrocarbon radicals having one or more double bonds connecting two carbon atoms, wherein said hydrocarbon radical may have straight, branched or cyclic moieties or combinations thereof. Examples of "alkenyl" groups include, but are not limited to, ethenyl, propenyl, butenyl, pentenyl, and dimethylpentyl, and include E and Z forms where applicable.

The term "aryl", as used herein, unless otherwise indicated, includes an aromatic ring system with no heteroatoms, which can be either unsubstituted or substituted with one, two or three substituents selected from the group consisting of halo, ($C_1$–$C_4$)alkyl optionally substituted with from one to three fluorine atoms and ($C_1$–$C_4$) alkoxy optionally substituted with from one to three fluorine atoms.

The term "heteroaryl", as used herein, unless otherwise indicated, includes an aromatic heterocycle containing five or six ring members, of which from 1 to 4 can be heteroatoms selected, independently, from N, S and O, and which rings can be unsubstituted, monosubstituted or disubstituted with substituents selected, independently, from the group consisting of halo, ($C_1$–$C_4$)alkyl, and ($C_1$–$C_4$)alkoxy, optionally substituted with from one to three fluorine atoms.

The term "one or more substituents", as used herein, refers to a number of substituents that equals from one to the maximum number of substituents possible based on the number of available bonding sites.

The terms "halos" and "halogen", as used herein, unless otherwise indicated, include, fluoro, chloro, bromo and iodo.

The term "treating", as used herein, refers to reversing, alleviating, inhibiting the progress of, or preventing the disorder or condition to which such term applies, or preventing one or more symptoms of such condition or disorder. The term "treatment", as used herein, refers to the act of treating, as "treating" is defined immediately above.

"Modulating serotonergic neurotransmission," as used herein, refers to increasing or improving, or decreasing or retarding the neuronal process whereby serotonin is released by a pre-synaptic cell upon excitation and crosses the synapse to stimulate or inhibit the post-synaptic cell.

Unless indicated to the contrary, when used herein the term "active compounds" and "active agents" are synonymous and are therefore interchangeable. This term refers to the compounds of Formula I or its pharmaceutically acceptable salts thereof either alone or in combination with one or more of the compounds selected from the group consisting of 5HT1D receptor antagonists, NK1 receptor antagonists, 5HT7 receptor antagonists or pharmaceutically acceptable salts of any of the compounds identified herein.

DETAILED DESCRIPTION OF THE INVENTION

Compounds of Formula I may be prepared according to the following reaction schemes and discussion. Unless otherwise indicated, $R^1$, $R^2$, $R^3$, $R^4$ and n, and structural Formulae I through IX in the reaction schemes and discussion that follow are as defined above.

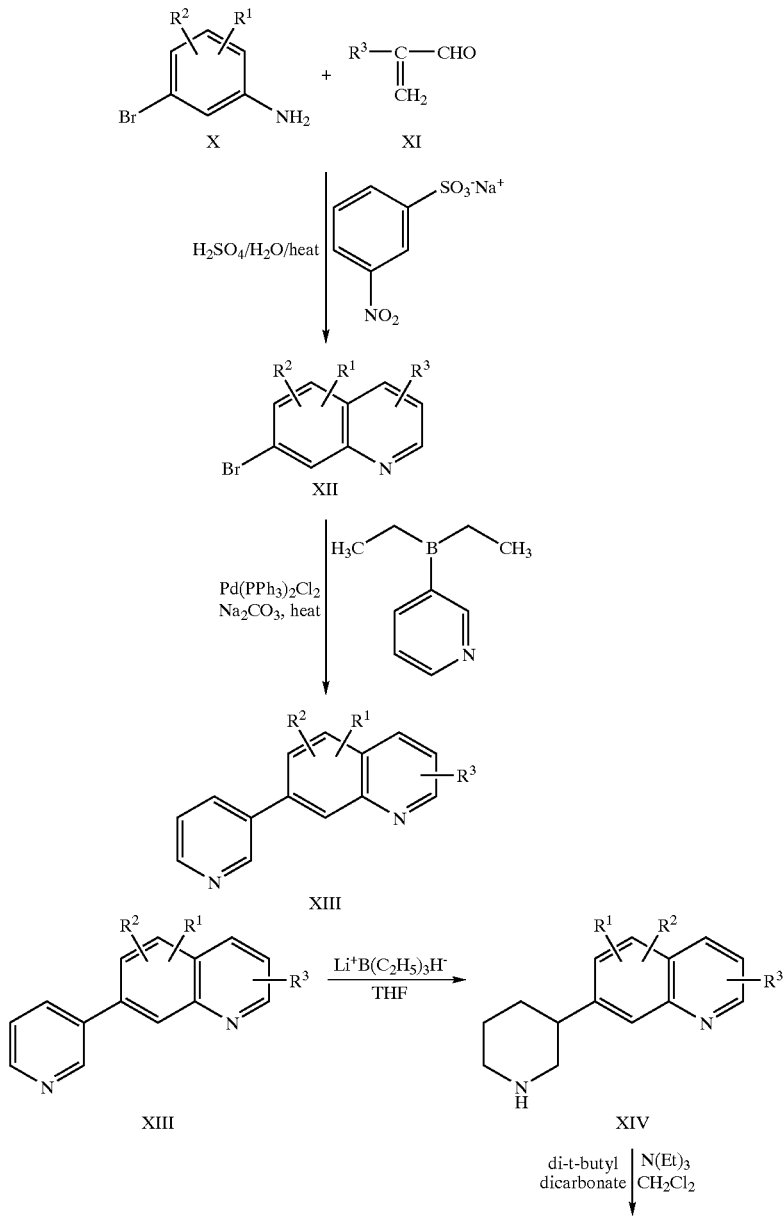

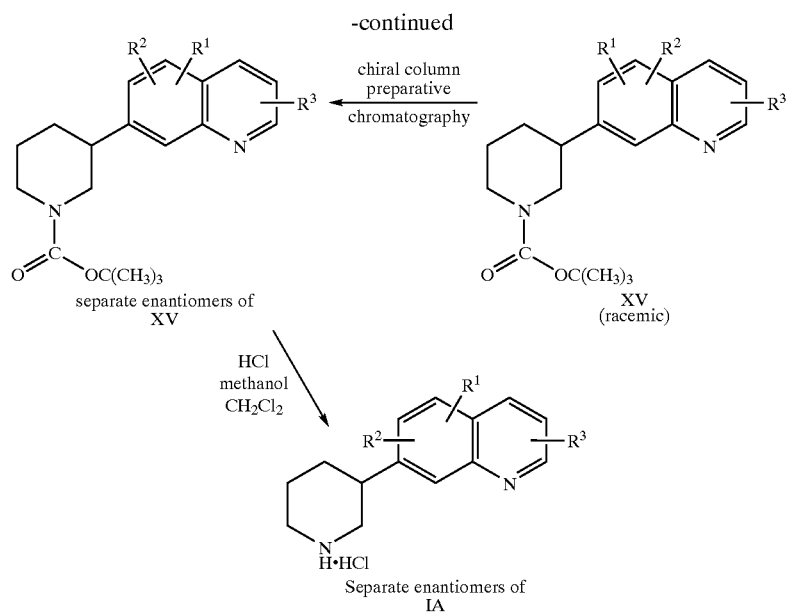
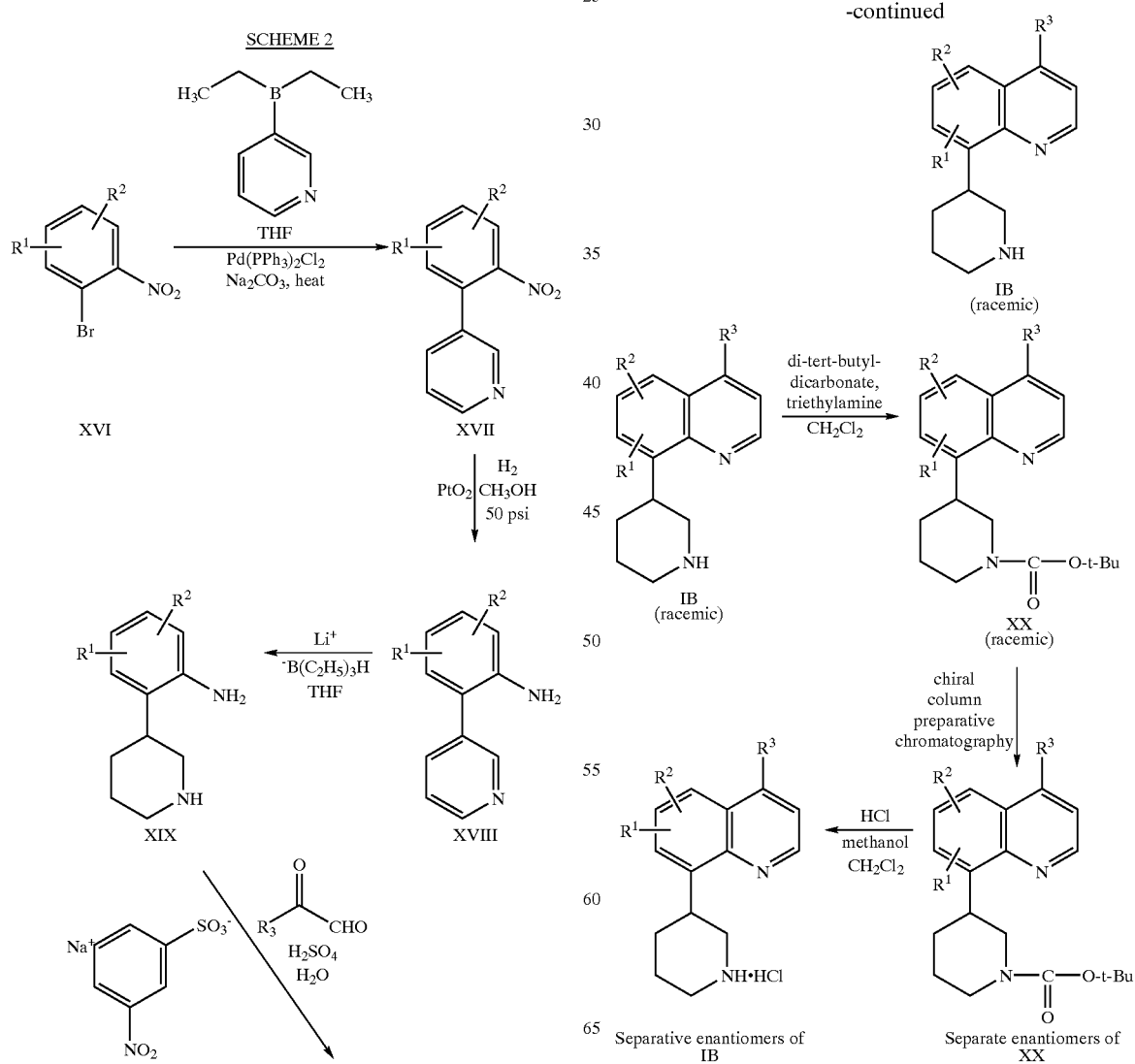

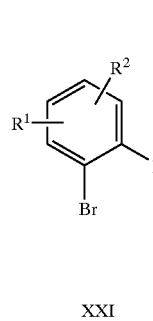
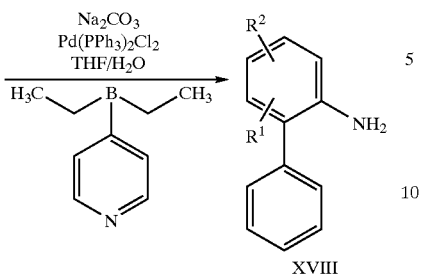
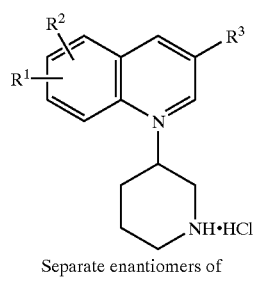
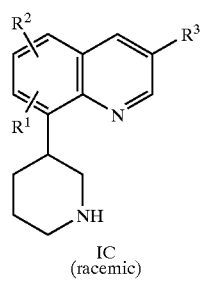
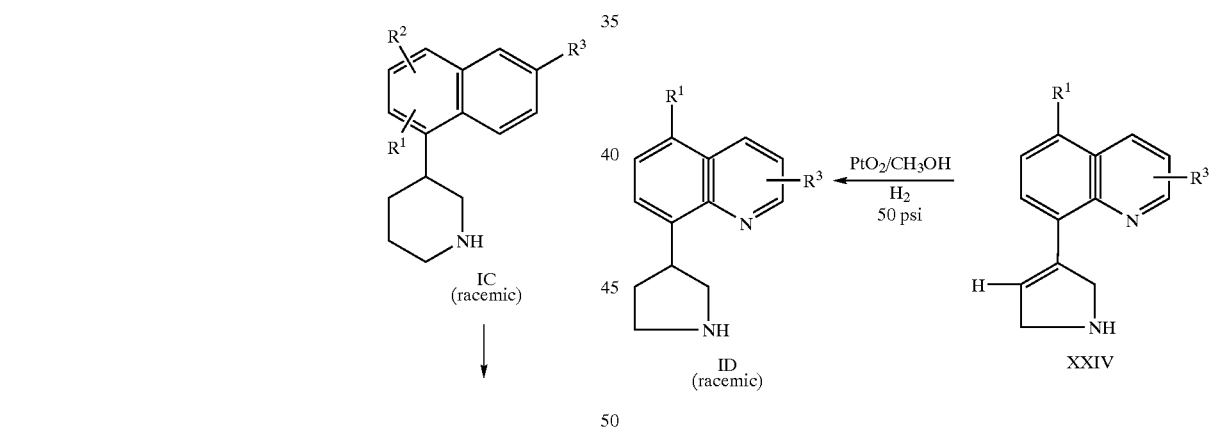
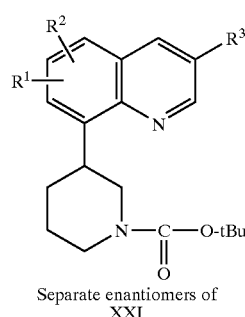
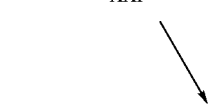
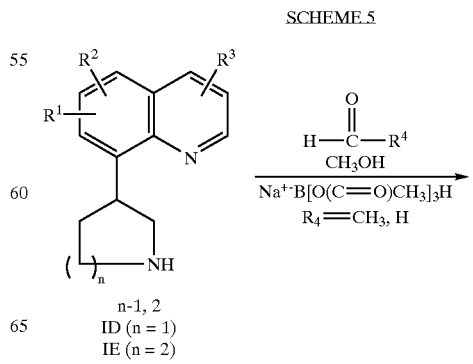

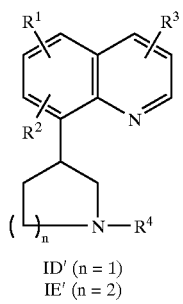

ID' (n = 1)
IE' (n = 2)

Scheme 1 illustrates the synthesis of compounds of the Formula I wherein $R^4$ is hydrogen, n is two, and the saturated nitrogen containing ring is piperidin-3-yl and is attached to position "7" of the quinoline nucleus. Referring to Scheme 1, a compound of Formula X is reacted with a compound of the Formula XI and 3-nitrobenzenesufonic acid or salt thereof, such as the Group IA salt, e g., sodium salt thereof in aqueous acid, e.g., sulfuric acid, at a temperature from about 100° C., to about 140° C., preferably at 110° C., to form the corresponding quinoline derivative of Formula XII. An alcohol, $R^3$—OH, may be used instead of the reactant XI. Reaction of the resulting compound of Formula XII with palladium triphenylphosphine dichloride and diethyl (3-pyridyl) borane in the presence of sodium carbonate or other inorganic basesuch as potassium carbonate, calcium carbonate, or cesium carbonatein an organic solvent such as, tetrahydrofuran (THF), 1,4-dioxane or 1,2-dichloroethane, and the like, preferably THF, at a temperature ranging from about 80° C. to about 120° C., preferably at about 90° C., yields the corresponding compound of Formula XIII.

Reduction of the pyridine derivative of Formula XIII using lithium triethylborohydride in tetrahydrofuran (THF) yields the corresponding piperidine derivative of Formula XIV. This reaction is typically carried out at a temperature from about 0° C. to about 70° C., preferably at about room temperature. Alternate reducing agents and solvents can be used. These are well known to those of ordinary skill in the art (e.g., lithium tri-isobutylborohydride, lithium triphenyl borohydride, and the like.). Lithium triphenyl borohydride in THF is preferred.

The piperidine derivative of Formula XIV is then converted into the corresponding ester of Formula XV by reacting it with di-t-butyldicarbonate in the presence of a tertiary amine base such as triethylamine, 4-methyl morpholine, or DBU (1,8-diazabicyclo[5.4.0.]undec-7-ene preferably triethylamine. Suitable solvents for this reaction include chloro alkanes (e.g., methylene chloride), 1,4-dioxane, THF and 1,2-dichloroethane. Methylene chloride is preferred. The reaction temperature can range from about 0° C. to about 50° C., and is preferably about 25° C.

Chiral column chromatography can be used to separate the enantiomers that comprise the racemic compound of Formula XV. Each enantiomer ester can then be deprotected using methods well known to those of skilled in the art, for example, by hydrolysis with a strong acid such as hydrochloric acid, sulfuric acid, acetic acid or trifluoroacetic acid, in a solvent such as methanol, methylene chloride, dioxane, ethyl ether, or ethyl acetate, to form the corresponding enantiomeric acid salt of a compound of the Formula IA. Preferably, hydrochloric acid is used. This reaction is typically carried out at a temperature from about 0° C. to about 70° C., and is preferably carried out at about room temperature.

Scheme 1 can also be used to prepare compounds Identical to those of Formula IA but for the piperidine ring is being attached to the quinoline nucleus at position "8". This can be accomplished by replacing the starting material of Formula X with the analogous compound wherein the bromo and amino groups are ortho to each other. In synthesizing intermediates analogous to intermediate XII having the bromine in position "8" according to Scheme 1, use of an alcohol $R^3$—OH instead of a compound of formula XI is preferred.

Scheme 2 illustrates the synthesis of compounds of the Formula I wherein n is 2, $R^4$ is hydrogen, $R^3$ is attached to position "4" of the quinoline nucleus, and the saturated nitrogen containing ring of Formula I is a piperidin-3-yl ring that is attached to position "8" of such nucleus. Referring to Scheme 2, a compound of the Formula XVI is reacted with palladium triphenylphosphine dichloride and [diethyl (3-pyridyl) borane] in the presence of an inorganic base, e.g., metal carbonates such as sodium carbonate potassium carbonate, calcium carbonateor cesium carbonate, and the like, preferably sodium carbonate, in an organic solvent such as THF, 1,4-dioxaneor 1,2-dichloroethane, preferably THF, at a temperature from about 80° C. to about 120° C., preferably at about 90° C., to form the corresponding compound of Formula XVII. Reduction of the nitrobenzene derivative of Formula XVII yields the corresponding aniline derivative of Formula XVIII. This reduction can be accomplished using methods well known to those of skill in the art, e.g., reaction with hydrogen gas at a pressure of 50 psi, in a methanol solvent, in the presence of a platinum oxide catalyst. This reaction is typically conducted at a temperature from about zero to about 40° C., and is preferably conducted at about room temperature.

The resulting pyridine derivative of Formula XVIII is then reduced to form the corresponding piperidine derivative of Formula XIX using the methods described above, in the description of the reactions in Scheme 1, for reducing compounds of the Formula XIII. The desired compound of Formula IB can be prepared by reacting the compound of Formula XIX with a compound of the Formula $R^3$(C=CH) CHO and 3-nitrobenzenesulfonic acid sodium salt or ferric chloride hexahydrate and zinc chloride in an organic solvent such as ethanol, n-propanol, isopropanol and an acid, e.g., inorganic acid, such as sulfuric acid or hydrochloric acid or in an aqueous inorganic acid, such as, or aqueous sulfuric acid, and more preferably aqueous hydrochloric acid, at a temperature from about 60° C., to about 100° C., preferably at about 60° C. The racemic compound of Formula IB can be separated into its enantiomers as illustrated in Scheme 2 and described above for the preparation of the enantiomers of compounds of the Formula IA.

Scheme 3 illustrates the preparation of compounds of the Formula I wherein n is 2, $R^4$ is hydrogen, $R^3$ is attached to position "3" of the quinoline nucleus, and the saturated nitrogen containing ring of Formula I is a piperidin-3-yl ring that is attached to position "8" of such nucleus. Referring to Scheme 3, the compound of Formula XXI is reacted with palladium triphenylphosphine dichloride and [diethyl (3-pyridyl) borane] in the presence of sodium carbonate or another inorganic base such as potassium carbonate, calcium carbonate or cesium carbonatein an organic solvent such as tetrahydrofuran (THF), 1,4-dioxaneor 1,2-dichloroethane, preferably THF, at a temperature from about 80° C. to about 120° C., preferably at about 90° C., to form the corresponding compound of Formula XVIII.

The compound of Formula XVIII is then reacted with a compound of the Formula $R^3$(C=CH)CHO and sodium

[3-nitrobenzenesulfonic acid or salt thereof, especially metal salts thereof, such as the sodium salt or ferric chloride hexahydrate and zinc chloride] in an organic solvent such as an alcohol of 1–6 carbon atoms, e.g., ethanol, n-propanol, isopropanol, and an acid, e.g., inorganic acid, e.g., aqueous inorganic acid, such as hydrochloric acid, sulfuric acid, preferably aqueous hydrochloric acid and more preferably aqueous, sulfuric acid, at a temperature from about 100° C., to about 140° C., preferably at about 110° C., to form the racemic pyridine substituted quinoline derivative of Formula XXII. Reduction of the pyridine substituted quinoline derivative of Formula XXII using lithium triethylborohydride in tetrahydrofuran (THF) yields the corresponding piperidine substituted quinoline derivative of Formula IC. This reaction is typically carried out at a temperature from about 0° C. to about 70° C., preferably at about 25° C. Alternate reducing agents and solvents can be used. These are well known to those of ordinary skill in the art.

The racemic compound of Formula IC can be separated into its enantiomers as illustrated in Schemes 1, 2 and 3 and described above for the preparation of the enantiomers of compounds of the Formula IA.

Scheme 4 illustrates the syntheses of compounds of the Formula I wherein n is 1, $R^4$ and $R^2$ are hydrogen, and $R^1$ is attached to position "5" of the quinoline nucleus. Referring to Scheme 4, the compound of Formula IVA is reacted with [3-oxo-pyrrolidine-1-carboxylic acid tert-butyl ester] and n-butyl lithium in an organic solvent such as tetrahydrofuran (THF), diethyl ether or 1,4-dioxane, preferably THF, at a temperature from about –77° C. to about –100° C., preferably at about –77° C., to form the corresponding compound of Formula XXIII. The addition of acid thereto followed by a basic workup hydrolyzed the amide to form the pyrrolene XXIV. The resulting compound of Formula XXIV can be reduced to form the corresponding racemic compound of Formula ID. This reduction can be accomplished using methods well known to those of ordinary skill in the art, e.g., reaction with hydrogen gas at a pressure of 50 psi, in a solvent such as acetic acid, methanol or ethanol, in the presence of a platinum oxide catalyst. Acetic acid is preferred for reduction of the free base pyrrolene to the free base pyrrolidine, while methanol or ethanol is preferred for reducing the hydrochloride salt of the pyrrolene to the hydrochloride salt of the pyrrolidine. This reaction is typically conducted at a temperature from about zero to about 40° C., and is preferably conducted at about room temperature.

Scheme 4 can also be used to prepare compounds identical to those of Formula ID but for the fact that the pyrrolidine ring is attached to the quinoline nucleus at position "7". This can be accomplished by replacing the starting material of Formula IVA with the analogous compound wherein the bromo group is attached to the quinoline ring at position "7".

Scheme 5 illustrates the formation of compounds of the Formula I wherein $R^4$ is other than hydrogen from the corresponding compounds of the Formula I wherein $R^4$ is hydrogen. Referring to Scheme 5, the compound of Formula IE or 1F is reacted with a compound of the Formula HC(=O)$R^4$ and an alkylating agent such as sodium triacetoxyborohydride, sodium cyanoborhydride and the like in an organic solvent especially an alcohol such as ethanol, or methanol, preferably methanol, at a temperature from about 0° C. to about 30° C., preferably about 25° C., to form the corresponding compound of Formula IE' or IF', respectively. The procedure illustrated in Scheme 5 can be used generally to convert compounds of the Formula I wherein $R^4$ is other than hydrogen into the corresponding compounds wherein $R^4$ is hydrogen.

The racemic compounds of Formula ID, ID', IE and IE' can be separated into its enantiomers as illustrated in Schemes 1, 2 and 3 and described above for the preparation of the enantiomers of compounds of the Formula IA.

Unless indicated otherwise, the pressure of each of the above reactions is not critical. Generally, the reactions will be conducted at a pressure of about one to about three atmospheres, preferably at ambient pressure (about one atmosphere).

The compounds of Formula I that are basic in nature are capable of forming a wide variety of different salts with various inorganic and organic acids. Although such salts must be pharmaceutically acceptable for administration to animals, it is often desirable in practice to initially isolate a compound of the Formula I from the reaction mixture as a pharmaceutically unacceptable salt and then simply convert the latter back to the free base compound by treatment with an alkaline reagent, and subsequently convert the free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent such as methanol or ethanol. Upon careful evaporation of the solvent, the desired solid salt is obtained.

The acids which are used to prepare the pharmaceutically acceptable acid addition salts of the base compounds of this invention are those which form non-toxic acid addition salts, i.e., salts containing pharmacologically acceptable anions, such as hydrochloride, hydrobromide, hydroiodide, nitrate, sulfate or bisulfate, phosphate or acid phosphate, acetate, lactate, citrate or acid citrate, tartrate or bitartrate, succinate, maleate, fumarate, gluconate, saccharate, benzoate, methanesulfonate and pamoate [i.e., 1,1'-methylene-bis-(2-hydroxy-3-naphthoate)] salts.

It will be appreciated that when using any of the combination methods of the present invention, referred to above, whichever components (a) and (b) that are utilized, i.e., whichever combination of a compound of Formula I or pharmaceutically acceptable salt thereof and 5HT1D receptor antagonist or salt, NK1 receptor antagonist or salt or sertonin reuptake inhibitor or salt, the combination will be administered to a patient within a reasonable period of time. The compounds may be in the same pharmaceutically acceptable carrier and therefore administered simultaneously. They may be in separate pharmaceutical carriers such as conventional oral dosage forms that are taken simultaneously. The term combination, as used above, also refers to the case where the pharmaceutically active compounds are provided in separate dosage forms and are administered sequentially. Therefore, by way of example, the NK1 receptor antagonist may be administered as a tablet and then, within a reasonable period of time, the compound of the Formula I may be administered either as an oral dosage form such as a tablet or a fast-dissolving oral dosage form. By a "fast dissolving oral formulation" is meant, an oral delivery form which when placed on the tongue of a patient, dissolves within about seconds.

Examples of serotonin reuptake inhibitors that can be used in the methods and compositions of this invention are sertraline, fluoxetine and paroxetine. Sertraline, (1S-cis)-4-(3,4-dichlorophenyl)-1,2,3,4-tetrahydro-N-methyl-1- naphthalenamine, has the chemical formula $C_{17}H_{17}NCl_2$ and the following structural formula

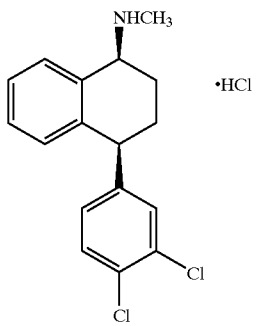

Its synthesis is described in U.S. Pat. No. 4,536,518, assigned to Pfizer Inc., the contents of which are incorporated by reference. Sertraline hydrochloride is useful as an antidepressant and anorectic agent, and is also useful in the treatment of depression, chemical dependencies, anxiety obsessive compulsive disorders, phobias, panic disorder, post traumatic stress disorder, and premature ejaculation.

Examples of NK-1 receptor antagonists that may be used in the methods and pharmaceutical compositions of this invention are compounds of the Formula

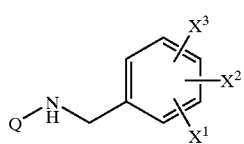

IX wherein $X^1$ is hydrogen, $(C_1-C_{10})$ alkoxy optionally substituted with from one to three fluorine atoms or $(C_1-C_{10})$ alkyl optionally substituted with from one to three fluorine atoms;

$X^2$ and $X^3$ are independently selected from hydrogen, halo, nitro, $(C_1-C_{10})$ alkyl optionally substituted with from one to three fluorine atoms, $(C_1-C_{10})$ alkoxy optionally substituted with from one to three fluorine atoms, trifluoromethyl, hydroxy, phenyl, cyano, amino, $(C_1-C_6$-alkylamino, di-$(C_1-C_6)$alkylamino, —C(=O)—NH—$(C_1-C_6)$alkyl, $(C_1-C_6)$ alkyl-C(=O)—NH—$(C_1-C_6)$ alkyl, hydroxy$(C_1-C_4)$alkyl, $(C_1-C_4)$alkoxy$(C_1-C_4)$alkyl, —NHC(=O)H and —NHC(=O)—$(C_1-C_6)$ alkyl; and Q is a group of the Formula

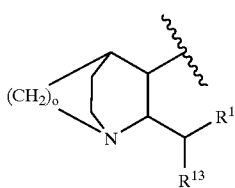

II

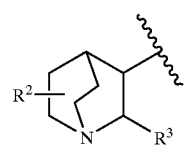

III

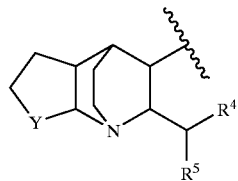

IV

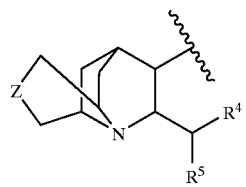

V

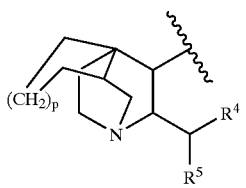

VI

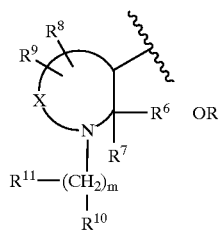

VII OR

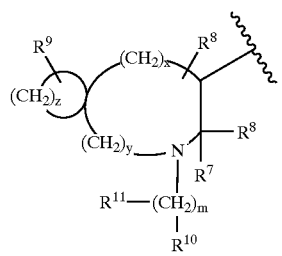

VIII wherein $R^1$ is a radical selected from furyl, thienyl, pyridyl, indolyl, biphenyl and phenyl optionally substituted with one or two substituents independently selected from halo, $(C_1-C_{10})$ alkyl optionally substituted with from one to three fluorine atoms, $(C_1-C_{10})$ alkoxy optionally substituted with from one to three fluorine atoms, carboxy, benzyloxycarbonyl and $(C_1-C_3)$ alkoxy-carbonyl;

$R^{13}$ is selected from $(C_3-C_4)$ branched alkyl, $(C_5-C_6)$ branched alkenyl, $(C_5-C_7)$ cycloalkyl, and the radicals named in the definition of $R^1$;

$R^2$ is hydrogen or $(C_1-C_5)$ alkyl;

$R^3$ is phenyl, biphenyl, naphthyl, pyridyl, benzhydryl, thienyl or furyl, and $R^3$ may optionally be substituted with from one to three substituents independently selected from halo, $(C_1-C_{10})$ alkyl optionally substituted with from one to three fluorine atoms and $(C_1-C_{10})$ alkoxy optionally substituted with from one to three fluorine atoms;

Y is $(CH_2)_l$ wherein l is an integer from one to three, or Y is a group of the Formula

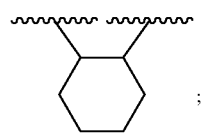

Z is oxygen, sulfur, amino, $(C_1-C_3)$alkylamino or $(CH_2)_n$ wherein n is zero, one or two;

o is two or three;

p is zero or one;

x is an integer from zero to four;

y is an integer from zero to four;

z is an integer from one to six, and the ring in Formula VIII containing $(CH_2)_z$ may contain from zero to three double bonds, and one of the carbons of said $(CH_2)_z$ may optionally be replaced by oxygen, sulphur or nitrogen;

$R^4$ is furyl, thienyl, pyridyl, indolyl, biphenyl, or phenyl optionally substituted with one or two substituents independently selected from halo, $(C_1-C_{10})$ alkyl optionally substituted with from one to three fluorine atoms, $(C_1-C_{10})$ alkoxy optionally substituted with from one to three fluorine atoms, carboxy, $(C_1-C_3)$ alkoxy-carbonyl and benzyloxycarbonyl;

$R^5$ is thienyl, biphenyl or phenyl optionally substituted with one or two substituents independently selected from halo, $(C_1-C_{10})$ alkyl optionally substituted with from one to three fluorine atoms and $(C_1-C_{10})$ alkoxy optionally substituted with from one to three fluorine atoms;

X is $(CH_2)_q$ wherein q is an integer from 1 to 6, and wherein any one of the carbon—carbon single bonds in said $(CH_2)_q$ may optionally be replaced by a carbon—carbon double bond, and wherein any one of the carbon atoms of said $(CH_2)_q$ may optionally be substituted with $R^8$, and wherein any one of the carbon atoms of said $(CH_2)_q$ may optionally be substituted with $R^9$;

m is an integer from 0 to 8, and any one of the carbon—carbon single bonds of $(CH_2)_m$ may optionally be replaced by a carbon—carbon double bond or a carbon—carbon triple bond, and any one of the carbon atoms of said $(CH_2)_m$ may optionally be substituted with $R^{11}$;

$R^6$ is a radical selected from hydrogen, $(C_1-C_6)$ straight or branched alkyl, $(C_3-C_7)$ cycloalkyl wherein one of the carbon atoms may optionally be replaced by nitrogen, oxygen or sulfur; aryl selected from biphenyl, phenyl, indanyl and naphthyl; heteroaryl selected from thienyl, furyl, pyridyl, thiazolyl, isothiazolyl, oxazolyl, isoxazolyl, triazolyl, tetrazolyl and quinolyl; phenyl $(C_2-C_6)$ alkyl, benzhydryl and benzyl, wherein each of said aryl and heteroaryl groups and the phenyl moieties of said benzyl, phenyl $(C_2-C_6)$ alkyl and benzhydryl may optionally be substituted with one or more substituents independently selected from halo, nitro, $(C_1-C_{10})$ alkyl optionally substituted with from one to three fluorine atoms, $(C_1-C_{10})$ alkoxy optionally substituted with from one to three fluorine atoms, amino, hydroxy-$(C_1-C_6)$alkyl, $(C_1-C_6)$alkoxy-$(C_1-C_6)$alkyl, $(C_1-C_6)$-alkylamino, $(C_1-C_6)$alkyl-O—C(=O)—, $(C_1-C_6)$ alkyl-O—C(=O)— $(C_1-C_6)$alkyl, $(C_1-C_6)$ alkyl-C(=O)—O—, $(C_1-C_{10})$alkyl-C(=O)—$(C_1-C_6)$alkyl-O—, $(C_1-C_6)$alkyl-C(=O)—, $(C_1-C_6)$ alkyl-C(=O)— $(C_1-C_6)$alkyl-, di-$(C_1-C_6)$alkylamino, —C(=O)NH—$(C_1-C_6)$alkyl, $(C_1-C_6)$-alkyl-C(=O)—NH—$(C_1-C_6)$alkyl, —NHC(=O)H and —NHC(=O)—$(C_1-C_6)$ alkyl; and wherein one of the phenyl moieties of said benzhydryl may optionally be replaced by naphthyl, thienyl, fury or pyridyl;

$R^7$ is hydrogen, phenyl or $(C_1-C_6)$alkyl;

or $R^6$ and $R^7$, together with the carbon to which they are attached, form a saturated carbocyclic ring having from 3 to 7 carbon atoms wherein one of said carbon atoms may optionally be replaced by oxygen, nitrogen or sulfur;

$R^8$ and $R^9$ are each independently selected from hydrogen, hydroxy, halo, amino, oxo (=O), nitrite, hydroxy-$(C_1-C_6)$alkyl, $(C_1-C_6)$alkoxy-$(C_1-C_6)$alkyl, $(C_1-C_6)$alkylamino, di-$(C_1-C_6)$alkylamino, $(C_1-C_6)$ alkoxy, $(C_1-C_6)$alkyl-O—C(=O)—, $(C_1-C_6)$alkyl-O—C(=O)—$(C_1-C_6)$alkyl, $(C_1-C_6)_6$alkyl-C(=O)—O—, $(C_1-C_6)$alkyl-C(=O)—$(C_1-C_6)$alkyl-O—, $(C_1-C_6$alkyl-C(=O)—, $C_1-C_6)$alkyl-C(=O)—$(C_1-C_6)$alkyl-, and the radicals set forth in the definition of $R^6$;

$R^{10}$ is $NHCR^{12}$, $NHCH_2R^{12}$, $NHSO_2R^{12}$ or one of the radicals set forth in any of the definitions of $R^6$, $R^8$ and $R_9$;

$R^{11}$ is oximino (=NOH) or one of the radicals set forth in any of the definitions of $R^6$, $R^8$ and $R^9$; and $R^{12}$ is $(C_1-C_6)$alkyl, hydrogen, phenyl$(C_1-C_6)$alkyl or phenyl optionally substituted with $(C_1-C_6)$ alkyl; and with the proviso that (a) when m is 0, $R^{11}$ is absent, (b) neither $R^8$, $R^9$, $R_{10}$ nor $R^{11}$ can form, together with the carbon to which it is attached, a ring with $R^7$, (c) when Q is a group of the Formula VII, $R^8$ and $R^9$ cannot be attached to the same carbon atom, (d) when $R^8$ and $R^9$ are attached to the same carbon atom, then either each of $R^8$ and $R^9$ is independently selected from hydrogen, fluoro, $(C_1-C_6)$ alkyl, hydroxy-$(C_1-C_6)$alkyl and $(C_1-C_6)$alkoxy-$(C_1-C_6)$alkyl, or $R^8$ and $R^9$, together with the carbon to which they are attached, form a $(C_3-C_6)$ saturated carbocyclic ring that forms a spiro compound with the nitrogen-containing ring to which they are attached, (e) when neither $X^1$, $X^2$ nor $X^3$ is a fluorinated alkoxy group, at least one of $R^1$, $R^3$, $R^4$, $R^5$, $R^6$, $R^7$ and $R^{13}$ is an aryl group substituted with a fluorinated alkoxy group;

and the pharmaceutically acceptable salts thereof.

Additional examples include the following compounds (hereinafter referred to, collectively, as "the Group A compounds"):

(2S,3S)-3-(6-methoxy-3-trifluoromethyl-1,3-dihydroisobenzofuran-5-yl)methylamino-2-phenylpiperidine;

(2S,3S)-3-(6-methoxy-1-methyl-1-trifluoromethylisochroman-7-yl)methylamino-2-phenylpiperidine;

(2S,3S)-3-(6-methoxy-3-methyl-3-trifluoromethyl-1,3-dihydroisobenzofuran-5-yl)methylamino-2-phenylpiperidine;

(2S,3S)-3-(6-methoxy-3-phenyl-3-trifluoromethyl-1,3-dihydroisobenzofuran-5-yl)methylamino-2-phenylpiperidine;

(2S,3S)-3-[1-(6-methoxy-3-methyl-3-trifluoromethyl-1,3-dihydroisobenzofuran-5-yl)ethylamino]-2-phenylpiperidine;

(2S,3S)-3-[(1R)-6-methoxy-1-methyl-1-trifluoromethyl-isochroman-7-yl]methylamino-2-phenylpiperidine;

(2S,3S)-3-[(3R)-6-methoxy-3-methyl-3-trifluoromethyl-1,3-dihydroisobenzofuran-5-yl)methylamino-2-phenylpiperidine;
(2S,3S)-N-(5-ethyl-2-methoxyphenyl)methyl-2-diphenylmethyl-1-azabi-cyclo[2.2.2]-octan-3-amine;
(2S,3S)-N-(5-isopropyl-2-methoxyphenyl)methyl-2-diphenylmethyl-1-azabicyclo[2.2.2]-octan-3-amine;
(2S,3S)-N-(5-sec-butyl-2-methoxyphenyl)-methyl-2-diphenylmethyl-1-azabicyclo[2.2.2]-octan-3-amine;
(2S,3S)-N-(5-tert-butyl-2-methoxyphenyl)-methyl-2-diphenylmethyl-1-azabicyclo[2.2.2]-octan-3-amine; and
(2S,3S)-N-(5-methyl-2-methoxyphenyl)methyl-2-diphenylmethyl-1-azabicyclo[2.2.2]-octan-3-amine;
and pharmaceutically acceptable salts thereof.

Preferred methods of this invention include the above combination methods wherein the an NK1 receptor antagonist that is employed in such method is a compound of the Formula IX wherein $R^1$, $R^4$, $R^5$ and $R^7$ are phenyl, $R^2$ is hydrogen, $R^3$ is phenyl optionally substituted with chlorine, fluorine, ($C_1$–$C_6$) alkyl optionally substituted with from one to three fluorine atoms or ($C_1$–$C_6$) alkoxy optionally substituted with from one to three fluorine atoms, m is 0 and n is 3 or 4.

More specific preferred methods of this invention include the above combination methods wherein the NK1 receptor antagonist is a compound of the Formula IX selected from:
(2S,3S)-3-(5-tert-butyl-2-methoxybenzyl)amino-2-(3-trifluoromethoxyphenyl)piperidine;
(2S,3S)-3-(2-isopropoxy-5-trifluoromethoxybenzyl)amino-2-phenyl-piperidine;
(2S,3S)-3-(2-ethoxy-5-trifluoromethoxybenzyl)amino-2-phenyl-piperidine;
(2S,3S)-3-(2-methoxy-5-trifluoromethoxybenzyl)amino-2-phenylpiperidine;
(2S,3S)-3-(-5-tert-butyl-2-trifluoromethoxybenzyl)amino-2-phenylpiperidine;
2-(diphenylmethyl)-N-(2-methoxy-5-trifluoromethoxyphenyl)methyl-1-azabicyclo[2.2.2]octan-3-amine;
(2S,3S)-3-[5-chloro-2-(2,2,2-trifluoroethoxy)-benzyl]amino-2-phenylpiperidine;
(2S,3S)-3-(5-tert-butyl-2-trifluoromethoxybenzyl)amino-2-phenylpiperidine;
(2S,3S)-3-(2-isopropoxy-5-trifluoromethoxybenzyl)amino-2-phenylpiperidine;
(2S,3S)-3-(2-difluoromethoxy-5-trifluoromethoxybenzyl)-amino-2-phenylpiperidine;
(2S,3S)-2-phenyl-3-[2-[(2,2,2-trifluoroethoxybenzyl)-aminopiperidine; or
(2S,3S)-2-phenyl-3-(2-trifluoromethoxybenzyl)]aminopiperidine;
or a pharmaceutically acceptable salt thereof.

Other NK1 receptor antagonists useful in the present invention are selected from:
3-[N-(2-methoxy-5-trifluoromethoxybenzyl)-amino]-5,5-dimethyl-2-phenylpyrrolidine;
3-[N-(2-methoxy-5-trifluoromethoxy-benzyl)amino]-4,5-dimethyl-2-phenylpyrrolidine;
3-(2-cyclopropyloxy-5-trifuoromethoxybenzyl)amino-2-phenylpiperidine;
3-(2-cyclopropylmethoxy-5-trifluoromethoxybenzyl)amino-2-phenylpiperidine;
3-(2-difluoromethoxy-5-phenylbenzyl)amino-2-phenylpiperidine;
3-(5-cyclopropylmethoxy-2-difluoromethoxybenzyl)amino-2-phenylpiperidine;
3-(2-methoxybenzyl)amino-2-(3-trifluoromethoxyphenyl)piperidine;
3-(2-methoxy-5-trifluoromethoxybenzyl)amino-2-(3-trifluoromethoxyphenyl)piperidine;
2-phenyl-3-(5-n-propyl-2-trifluoromethoxybenzyl)amino-piperidine;
3-(5-isopropyl-2-trifluoromethoxybenzyl)amino-2-phenylpiperidine;
3-(5-ethyl-2-trifluoromethoxybenzyl)amino-2-phenyl-piperidine;
3-(5-sec-butyl-2-trifluoromethoxybenzyl)amino-2-phenyl-piperidine;
3-(5-difluoromethoxy-2-methoxybenzyl)amino-2-phenylpiperidine;
3-(2-methoxy-5-trifluoromethoxybenzyl)amino-2-phenylpyrrolidine;
3-(2-methoxy-5-trifluoromethoxybenzyl)amino-2-phenylhomopiperidine;
2-benzhydryl-3-(2-methoxy-5-trifluoromethoxy-benzyl)aminopyrrolidine;
2-benzhydryl-3-(2-methoxy-5-trifluoromethoxy-benzyl)aminohomopiperidine;
3-[2,5-bis-(2,2,2-trifluoroethoxy)benzyl]amino-2-phenylpiperidine;
2-phenyl-3-(3-trifluoromethoxybenzyl)aminopiperidine;
2-benzhydryl-3-(2-methoxy-5-trifluoromethoxybenzyl)-aminopiperidine;
1-(5,6-difluorohexyl)-3-(2-methoxy-5-trifluoromethoxybenzyl)amino-2-phenylpiperidine;
1-(6-hydroxyhexyl)-3-(2-methoxy-5-trifluoromethoxybenzyl)amino-2-phenylpiperidine;
3-phenyl-4-(2-methoxy-5-trifluoromethoxybenzyl)amino-2-azabicyclo[3.3.0]octane;
4-benzhydryl-5-(2-methoxy-5-trifluoromethoxybenzyl)amino-3-azabicyclo[4.1.0]heptane;
4-(2-methoxy-5-trifluoromethoxybenzyl)amino-3-phenyl-2-azabicyclo[4.4.0]decane;
2-phenyl-3-(2-methoxy-5-trifluoromethoxybenzyl)-aminoquinuclidine;
8-benzhydryl-N-(2-methoxy-5-trifluoromethoxybenzyl)-9-azatricyclo[4.3.1.0$^{4,9}$]decan-7-amine;
9-benzhydryl-N-(2-methoxy-5-trifluoromethoxybenzyl)-10-azatricyclo[4.4.1.0$^{5,10}$]undecan-8-amine;
9-benzhydryl-N-(2-methoxy-5-trifluoromethoxybenzyl)-3-thia-10-azatricyclo-[4.4.1.0$^{5,10}$]undecan-8-amine;
8-benzhydryl-N-(2-methoxy-5-trifluoromethoxybenzyl)-9-azatricyclo[4.3.1.0$^{4,9}$]decan-7-amine;
5,6-pentamethylene-2-benzhydryl-3-(2-methoxy-5-trifluoromethoxybenzyl)amino-quinuclidine;
5,6-trimethylene-2-benzhydryl-3-(2-methoxy-5-trifluoromethoxybenzyl)amino-quinuclidine;
9-benzhydryl-N-((2-methoxy-5-trifluoromethoxyphenyl)-methyl)-3-oxa-10-azatricyclo-[4.4.1.0$^{5,10}$]undecan-3-amine;
8-benzhydryl-N-((2-methoxy-5-trifluoromethoxyphenyl-methyl)-7-azatricyclo-[4.4.1.0$^{5,10}$]undecan-9-amine; and
2-benzhydryl-N-((2-methoxy-5-trifluoromethoxyphenyl)-methyl)-1-azabicyclo-[3.2.2]nonan-3-amine;
and pharmaceutically acceptable salts thereof.

Other more specific embodiments of the present invention relate to the above combination methods wherein the NK1 receptor antagonist that is employed in such methods is a compound of the Formula IX wherein o is two or three and each of $R^1$ and $R^{13}$ is phenyl or substituted phenyl.

Other more specific embodiments of the present invention relate to the above combination methods wherein the NK1 receptor antagonist that is employed in such methods is a compound of the Formula IX wherein Q is a group of the Formula III, $R^2$ is hydrogen and $R^3$ is phenyl or substituted phenyl.

Other more specific embodiments of the present invention relate to the above combination methods wherein the NK1 receptor antagonist that is employed in such methods is a compound of the Formula IX wherein Q is a group of the Formula IV wherein I is one or two and each of $R^4$ and $R^5$ is phenyl or substituted phenyl.

Other more specific embodiments of the present invention relate to the above combination methods wherein the NK1 receptor antagonist that is employed in such methods is a compound of the Formula IX wherein Q is a group of the Formula V wherein n is zero or one and each of $R^4$ and $R^5$ is phenyl or substituted phenyl.

Other more specific embodiments of the present invention relate to the above combination methods wherein the NK1 receptor antagonist that is employed in such methods is a compound of the Formula IX wherein Q is a group of the Formula VI wherein p is one and each of $R^4$ and $R^5$ are phenyl or substituted phenyl.

Other more specific embodiments of the present invention relate to the above combination methods wherein the NK1 receptor antagonist that is employed in such methods is a compound of the Formula IX wherein Q is a group of the Formula VII wherein q is two, three or four, m is zero and $R^6$ is phenyl or substituted phenyl.

Other more specific embodiments of the present invention relate to the above combination methods wherein the NK1 receptor antagonist that is employed in such methods is selected from:
(2S,3S)-3-(6-methoxy-1-methyl-1-trifluoromethylisochroman-7-yl)methylamino-2-phenylpiperidine;
(2S,3S)-3-[(1R)-6-methoxy-1-methyl-1-trifluoromethylisochroman-7-yl]methylamino-2-phenylpiperidine;
(2S,3S)-N-(5-isopropyl-2-methoxyphenyl)methyl-2-diphenylmethyl-1-azabicyclo[2.2.2]-octan-3-amine; and
(2S,3S)-N-(5-tert-butyl-2-methoxyphenyl)-methyl-2-diphenylmethyl-1-azabicyclo[2.2.2]-octan-3-amine;
and their pharmaceutically acceptable salts.

Examples of 5HT1 D antagonists that can be used in the pharmaceutical corn positions and methods of this invention are the following:
3-(4-chlorophenyl)-5-[2-(4-methylpiperazin-1-yl)-benzylidene]-imidazolidine-2,4-dione;
3-(4-chlorobenzyl-5-[2-(4-methylpiperazin-1-yl)-benzylidene]-imidazolidine-2,4-dione;
3-(4-chlorobenzyl)-5-[2-(4-methylpiperazin-1-yl)-benzylidene]-thiazolidine-2,4-dione;
4-benzyl-2-[2-(4-methylpiperazin-1-yl)-benzylidene]-thiomorpholin-3-one;
4-(3,4-dichlorobenzyl)-2-[2-(4-methylpiperazin-1-yl)-benzylidene]-thiomorpholin-3-one;
3-(4-chlorophenyl)-5-[2-(4-methylpiperazin-1-yl)-benzylidene]-thiazolidine-2,4-dione;
3-(4-trifluoromethylphenyl)-5-[2-(4-methylpiperazin-1-yl)-benzylidene]-thiazolidine-2,4-dione;
2-[2-(4-methylpiperazin-1-yl)-benzylidene]-4-(4-trifluoromethylphenyl)-thiomorpholin-3-one;
2-[2-(4-methylpiperazin-1-yl)-benzylidene]-thiomorpholin-3-one;
4-(3,4-dichlorophenyl)-2-[2-fluoro-6-(4-methylpiperazin-1-yl)-benzylidene]-thiomorpholin-3-one;
4-(3,4-dichlorophenyl)-2-[2-(4-methylpiperazin-1-yl)-benzylidene]-morpholin-3-one;
4-(3,4-dichlorophenyl)-2-[2-(4-methylpiperazin-1-yl)-benzylidene]-thiomorpholin-3-one;
4-(3,4-dichlorophenyl)-2-[2-(4-methylpiperazin-1-yl)-benzyl]-thiomorpholin-3-one;
4-methyl-2-[2-(4-methylpiperazin-1-yl)-benzylidene]-thiomorpholin-3-one; and
4-(3,4-dichlorophenyl)-2-(2-piperazin-1-ylbenzylidene)-thiomorpholin-3-one,
and pharmaceutically acceptable salts thereof.

Other specific NK1 receptor antagonists useful in the present invention include:
5-[2-(4-methylpiperazin-1-yl)-benzylidene]-thiazolidine-2,4-dione;
2-[2,4-dibromo-6-(4-methylpiperazin-1-yl)-benzylidene]-4-(3,4-dichlorophenyl)-thiomorpholin-3-one;
4-(4-chlorophenyl)-2-[2-(4-methylpiperazin-1-yl)-benzylidene]-[1,4]oxazepan-3-one;
4-(4-chlorophenyl)-2-[2-(4-methylpiperazin-1-yl)-benzylidene]-[1,4,5]oxadiazepan-3-one;
4-(4-chlorophenyl)-2-[2-(4-methylpiperazin-1-yl)-benzylidene]-[1,4]thiazepan-3-one;
4-(3,4-dichlorophenyl)-2-(2-[[(2-dimethylaminoethyl)-methyl-amino]-benzylidene)-thiomorpholin-3-one;
4-(3,4-dichlorophenyl)-2-[2-(1-methylpiperidin-4-yl)-benzylidene]-thiomorpholin-3-one;
4-(3,4-dichlorophenyl)-2-[2-(1,4-dimethylpiperidin-4-yl)-benzylidene]-thiomorpholin-3-one;
4-(3,4-dichlorophenyl)-2-[2-(4-methylpiperazin-1-yl)-benzylidene]-thiomorpholine-3,5-dione;
4-(3,4-dichlorophenyl)-2-[2-dimethylaminoethoxy)-benzylidene]-thiomorpholin-3-one;
4-(3,4-dichlorophenyl)-2-[2-(4-isopropylpiperazin-1-yl)-benzylidene]-thiomorpholin-3-one;
4-(3,4-dichlorophenyl)-2-[2-(1-methylpyrrolidin-3-ylmethyl]benzylidene]-thiomorpholin-3-one;
4-(3,4-dichlorophenyl)-2-{2-[methyl-(1-methylpyrrolidin-2-ylmethyl)-amino]-benzylidene}-thiomorpholin-3-one;
4-(3,4-dichlorophenyl)-2-[2-(1-methylpyrrolidin-2-ylmethoxy)-benzylidene]-thiomorpholin-3-one;
4-(3,4-dichlorophenyl)-2-{2-[2-(1-methylpyrrolidin-2-yl]ethyl]-benzylidene}-thiomorpholin-3-one;
1-(3,4-dichlorophenyl)-4-methyl-3-[2-(4-methylpiperazin-1-yl)-benzylidene]-piperazin-2-one;
4-methyl-3-[2-(4-methylpiperazin-1-yl)-benzylidene]-1-(4-trifluoromethylphenyl)-piperazin-2-one;
1-(4-chlorophenyl)-4-methyl-3-[2-(4-methylpiperazin-1-yl)-benzylidene]-piperazin-2-one;
2-[2-(4-methylpiperazin-1-yl)-benzylidene]-4-(4-trifluoromethylphenyl)-morpholin-3-one;
2-[4-fluoro-2-(4-methylpiperazin-1-yl)-benzylidene]-4-(4-trifluoromethylphenyl)-thiomorpholin-3-one;
2-[5-fluoro-2-(4-methylpiperazin-1-yl)-benzylidene]-4-(4-trifluoromethylphenyl)-thiomorpholin-3-one;
2-{1-[2-(4-methylpiperazin-1-yl)-phenyl]-ethylidene}-4-(4-trifluoromethylphenyl)-thiomorpholin-3-one;
2-[2-(4-methylpiperazin-1-yl)-benzyl]-4-(4-trifluoromethylphenyl)-thiomorpholin-3-one;
4-(4-chlorophenyl)-6-methyl-2-[2-(4-methylpiperazin-1-yl)-benzylidene]-thiomorpholin-3-one;
3-(4-chlorophenyl)-2,2-dimethyl-5-[2-(4-methylpiperazin-1-yl)-benzylidene]-thiazolidin-4-one;
4-(4-chlorophenyl)-2-[2-(4-methylpiperazin-1-yl)-benzylidene]-[1,4]oxazepan-3-one;
4-(4-chlorophenyl)-2-[2-(4-methylpiperazin-1-yl)-benzylidene]-4H-[1,4]thiazin-3-one;
1-(4-chlorophenyl)-4,6,6-trimethyl-3-[2-(4-methylpiperazin-1-yl)-benzylidene]-piperazin-2-one;
1-(4-chlorophenyl)-4-methyl-3-[2-(4-methylpiperazin-1-yl)-benzylidene]-piperazin-2-one;
4-(4-chlorophenyl)-2-[2-(4-methylpiperazin-1-yl)-benzylidene]-morpholin-3-one;
3-(4-chlorophenyl)-5-[2-(4-methylpiperazin-1-yl)-benzylidene]-oxazolidin-4-one;

3-(4-chlorophenyl)-2,2-dimethyl-5-[2-(4-methylpiperazin-1-yl)-benzylidene]-imidazolidin-4-one;
and pharmaceutically acceptable salts thereof.

The following references refer to quinuclidine, piperidine, ethylene diamine, pyrrolidine and azanorbornane derivatives and related compounds that exhibit activity as NK1 receptor antagonists and that can be used, in combination with the 5HT7 receptor partial agonists of the Formula I, in the pharmaceutical compositions and methods of this invention, and to methods of preparing the same: U.S. Pat. No. 5,162,339, which issued on Nov. 11, 1992; U.S. Pat. No. 5,232,929, which issued on Aug. 3, 1993; World Patent Application WO 92/20676, published Nov. 26, 1992; World Patent Application WO 93/00331, published Jan. 7, 1993; World Patent Application WO 92/21677, published Dec. 10, 1992; World Patent Application WO 93/00330, published Jan. 7, 1993; World Patent Application WO 93/06099, published Apr. 1, 1993; World Patent Application WO 93/10073, published May 27, 1993; World Patent Application WO 92/06079, published Apr. 16, 1992; World Patent Application WO 92/12151, published Jul. 23, 1992; World Patent Application WO 92/15585, published Sep. 17, 1992; World Patent Application WO 93/10073, published May 27, 1993; World Patent Application WO 93/19064, published Sep. 30, 1993; World Patent Application WO 94/08997, published Apr. 28, 1994; World Patent Application WO 94/04496, published Mar. 3, 1994; World Patent Application WO 95/07908, published Mar. 3, 1995; World Patent Application WO 94/20500, published September 15, 1994; World Patent Application WO 94/13663, published Jun. 23, 1994; World Patent Application WO 95/16679, published Jun. 22, 1995; World Patent Application WO 97/08144, published Mar. 6, 1997; World Patent Application WO 97/03066, published Jan. 30, 1997; World Patent Application WO 99/25714, published May 27, 1999; U.S. Pat. No. 988,653, filed Dec. 10, 1992; U.S. Pat. No. 026,382, filed Mar. 4, 1993; U.S. Pat. No. 123,306, filed Sep. 17, 1993, and U.S. Pat. No. 072,629, filed Jun. 4, 1993. All of the foregoing World Patent Applications designate the United States. The foregoing patents and patent applications are incorporated herein by reference in their entirety.

NK-1 receptor antagonists of the Formula IX can be prepared as described in the following patents and patent applications, all of which are referred to above and incorporated herein by reference in their entirety: WO 93/00331, WO 92/21677, WO 92/15585, WO 92/01688, WO 93/06099, WO 91/18899, U.S. Pat. No. 5,162,339, and U.S. Pat. No. 5,232,929.

Other NK1 receptor antagonists that can be used, together with the 5HT7 agonists of the Formula I, for the treatment of anxiety or depression in accordance with the methods and pharmaceutical compositions of the present invention are those compounds and pharmaceutically acceptable salts described in the following references: European Patent Application EP 499,313, published Aug. 19, 1992; European Patent Application EP 520,555, published Dec. 30, 1992; European Patent Application EP 522,808, published Jan. 13, 1993, European Patent Application EP 528,495, published Feb. 24, 1993, PCT Patent Application WO 93/14084, published Jul. 22, 1993, PCT Patent Application WO 93/01169, published Jan. 21, 1993, PCT Patent Application WO 93/01165, published Jan. 21, 1993, PCT Patent Application WO 93/01159, published Jan. 21, 1993, PCT Patent Application WO 92/20661, published Nov. 26, 1992, European Patent Application EP 517,589, published Dec. 12, 1992, European Patent Application EP 428,434, published May 22, 1991, and European Patent Application EP 360,390, published Mar. 28, 1990. All of the foregoing World Patent Applications designate the United States. The foregoing patents and patent applications are incorporated herein by reference in their entirety.

For any of the therapeutic methods or pharmaceutical compositions of the present invention, the appropriate dose regimen, the amount of each dose of an active agent administered, and the specific intervals between doses of each active agent will depend upon the subject being treated, the specific active agent being administered and the nature and severity of the specific disorder or condition being treated. In general, the active compounds of this invention, when used as a single active agent or in combination with another active agent, will be administered to an adult human in an amount from about 0.05 to about 1500 mg per day, in single or divided doses, preferably from about 5 to about 200 mg/day. Such compounds may be administered on a regimen of up to 6 times per day, preferably 1 to 4 times per day, especially 2 times per day and most especially once daily. Variations may nevertheless occur depending upon the species of animal being treated and its individual response to said medicament, as well as on the type of pharmaceutical formulation chosen and the time period and interval at which such administration is carried out. In some instances, dosage levels below the lower limit of the aforesaid range may be more than adequate, while in other cases still larger doses may be employed without causing any harmful side effect, provided that such larger doses are first divided into several small doses for administration throughout the day.

A proposed daily dose of a 5HT reuptake inhibitor, preferably sertraline, in the combination methods and compositions of this invention, for oral, parenteral or buccal administration to the average adult human for the treatment of the conditions referred to above, is from about 0.1 mg to about 2000 mg, preferably from about 1 mg to about 200 mg of the 5HT reuptake inhibitor per unit dose, which could be administered, for example, 1 to 4 times per day.

A proposed daily dose of a 5HT1D receptor antagonist in the combination methods and compositions of this invention, for oral, parenteral, rectal or buccal administration to the average adult human for the treatment of the conditions referred to above, is from about 0.01 mg to about 2000 mg, preferably from about 0.1 mg to about 200 mg of the 5HT1 D receptor antagonist per unit dose, which could be administered, for example, 1 to 4 times per day.

A proposed daily dose of an NK1 receptor antagonist in the combination methods and compositions, for oral, parenteral or buccal administration to the average adult human for the treatment of the conditions referred to above, is from about 0.1 mg to about 2000 mg, preferably from about 1 mg to about 200 mg of the NK1 receptor antagonist per unit dose which could be administered, for example, 1 to 4 times per day.

The 5HT7 receptor agonists, the NK1 receptor antagonists, the serotonin reuptake inhibitors and the 5HT1 D receptor antagonists, and their pharmaceutically acceptable salts, that are employed in the pharmaceutical compositions and methods of this invention are hereinafter also referred to as "therapeutic agents". The therapeutic agents can be administered via either the oral, buccal, nasal or parenteral route. Compositions containing both a 5HT7 receptor agonist and an NK1 receptor antagonist, a 5HT1 D receptor antagonist or a serotonin reuptake inhibitor, will generally be administered orally or parenterally daily, in single or divided doses, so that the total amount of each active agent administered falls within the above guidelines.

The therapeutic agents may be administered alone or in combination with pharmaceutically acceptable carriers or diluents by either of the routes previously indicated, and such administration may be carried out in single or multiple doses. More particularly, the therapeutic agents of this invention can be administered in a wide variety of different dosage forms, i.e., they may be combined with various pharmaceutically acceptable inert carriers in the form of tablets, capsules, lozenges, troches, hard candies, suppositories, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the therapeutic agents of this invention, when administered separately (i.e., not in the same pharmaceutical composition) are present in such dosage forms at concentration levels ranging from about 5.0% to about 70% by weight.

For oral administration, the pharmaceutical compositions may take the form of, for example, tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); and preservatives (e.g., methyl or propyl p-hydroxybenzoates or sorbic acid).

For preparing solid compositions such as tablets, the principal active ingredient is mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a therapeutic agent, or a non-toxic pharmaceutically acceptable salt thereof. When referring to these preformulation compositions as homogeneous, it is meant that the therapeutic agent is dispersed evenly throughout the composition so that the composition may be readily subdivided into equally effective unit dosage forms such as tablets, pills and capsules. This solid preformulation composition is then subdivided into unit dosage forms of the type described above containing, typically, from 0.05 to about 500 mg of each of the therapeutic agents contained in the composition. The tablets or pills of the composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac acetyl alcohol and cellulose acetate.

For buccal administration, the composition may take the form of tablets or lozenges formulated in conventional manner.

The therapeutic agents may be formulated for parenteral administration by injection, including using conventional catheterization techniques or infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulating agents such as suspending, stabilizing and/or dispersing agents. Solutions of a therapeutic agent in either sesame or peanut oil or in aqueous propylene glycol may be employed. The aqueous solutions should be suitably buffered if necessary and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art. Alternatively, the active ingredient may be in powder form for reconstitution with a suitable vehicle, e.g., sterile pyrogen-free water, before use.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the invention and a suitable powder base such as lactose or starch.

Aerosol formulations of the active compounds of this invention for treatment of the conditions referred to above in the average adult human are preferably arranged so that each metered dose or "puff" of aerosol contains 20 $\mu$g to 1000 $\mu$g of active compound. The overall daily dose with an aerosol will be within the range 100 $\mu$g to 10 mg. Administration may be several times daily, for example 2, 3, 4 or 8 times, giving for example, 1, 2 or 3 doses each time.

The compounds of Formula I may advantageously be used in conjunction with one or more other therapeutic agents, for instance, different antidepressant agents such as tricyclic antidepressants (e.g., amitriptyline, dothiepin, doxepin, trimipramine, butripyline, clomipramine, desipramine, imipramine, iprindole, lofepramine, nortriptyline or protriptyline), or monoamine oxidase inhibitors (e.g., isocarboxazid, phenelzine or tranylcypromine), and/or with antiparkinsonian agents such as dopaminergic antiparkinsonian agents (e.g., levodopa, preferably in combination with a peripheral decarboxylase inhibitor e.g., benserazide or carbidopa, or with a dopamine agonist e.g., bromocriptine, lysuride or pergolide). It is to be understood that the present invention covers the use of a compound of general Formula I or a physiologically acceptable salt or solvate thereof in combination with one or more other therapeutic agents.

The affinities of the active compounds for 5HT7 receptors can be determined using standard radioligand binding assays as described in the literature. The 5HT7 affinity can be measured using the following procedure.

$^3$H-5-Carboxamidotryptamine ($^3$H-5-CT) Binding to Rat 5HT7 Receptors Expressed in HEK-293 Cells:

Materials:
HEK-293 cells expressing the rat 5-HT7 receptor
Brinkman Polytron Tissue Homogenizer
Phosphate Buffered Saline (GIBCO)
Capped Centrifuge Tubes
Centrifuge
50 mMTris HClBuffer, pH7.7 (SigmaT-4378)
EDTA (Sigma E-4884)
$MgSO_4$ (Sigma M-7506)
$CaCl_2$ (MCBCX 156)
pargyline (SigmaP-8013)
ascorbicacid (Calbiochem 1831)
5-HTcreatinine sulfate complex (Sigma H-7752)
$^3$H-5CT (Amersham TRK. 1038)
12×75 mm boroscilicate glass tubes
96 well V-bottom polypropylene plates (NUNC-442587)
Skatron 96 Well Harvester
Whatman GF/B Glass Fiber Filters (Brandel FP-105) presoaked in 0.3% polyethylenimine (Sigma-P-3143)
Betaplate scintillation counter (Wallac/LKB)

Tissue Preparation:
HEK-293 cells expressing 5HT7 receptors are grown according to standard cell culture techniques. Cells are harvested by removing the media, rinsing the flasks out with phosphate buffered saline (PBS) and then allowed to sit for 2–3 minutes with PBS containing 2.5 mM EDTA. Cells are dislodged and poured into a RcappableS centrifuge tube. Flasks are rinsed with PBS and added to a centrifuge tube. The cells are centrifuged for ten minutes at 40,000×g (20,000 rpm in a Sorvall SS34 rotor). The supernatant is discarded and at this point the remaining pellet is weighed and can be stored frozen (−20 degrees C.) until used in the binding assay. Pellets (fresh or frozen) are homogenized in 50 mM Tris HCl buffer (pH 7.4 at 4 degrees C.) using a Polytron homogenizer (setting 15,000 rpm) for ten seconds in a biolgcial hood certified for use with human tissues. The homogenate is centrifuged for ten minutes at 40,000×g. The supernatant is discarded and the pellet resuspended with the Polytron in a fresh ice-cold 50 mM Tris HCl (pH 7.4 at 4 degrees) buffer and centrifuged again. The final pellet is resuspended in assay buffer (50 mM Tris HCl buffer (pH 7.7 at 25 degrees) containing 0.5 mM EDTA, 10 mM $MgSO_4$, 2 mM $CaCl_2$) for a final tissue concentration of 5–15 mg wet weight of original pellet per mL buffer (2× final concentration).

Receptor Binding
Incubation is initiated by the addition of tissue to V-bottom polypropylene plates (in triplicate). Incubation is at 25 degrees C. for 2 hours.

Each tube receives:
100 uL tissue suspension (5–15 mg/mL original wet weight), 50 uL $^3$H-5-CT** (0.4 nM final concentration), and 50 uL drug or buffer

**$^3$H-5-CT is made up in assay buffer that contains 40 uM pargyline & 0.4% ascorbic acid (for final concentrations of 10 uM pargyline & 0.1% ascorbic acid).

Nonspecific binding is determined using 1 uM 5-HT creatinine sulfate. Incubation is ended by rapid filtration under vacuum through fire-treated Whatman GF/B glass fiber filters (presoaked in 0.3% PEI for two hours and dried) using a 96 well Skatron Harvester (3 sec prewet; 20 seconds wash; 15 seconds dry). Filters are put into LKB sample bags with 10 mL BetaScint. Radioactivity is quantified by liquid scintillation counting using a BetaPlate counter (LKB).

The percent inhibition of specific binding is calculated for each concentration of test compound. An $IC_{50}$ value (the concentration which inhibits 50% of the specific binding) is determined by linear regression of the concentration-response data (log concentration vs. logit percent values). Ki values are calculated according to Cheng & Prusoff: $Ki=IC_{50}/(1+(L/Kd))$, where L is the concentration of the radioligand used in the experiment and the Kd value is the dissociation constant for the radioligand determined in separate saturation experiments. The binding activities to 5HT7 receptors of approximately 40 compounds of the invention that were assayed as described above ranged from about 3.5 nM to about 5 μM. For example the title compound of Example 8, below, showed a Ki of about 7.6 nM, and the title compound of Example 10, below, showed a Ki of about 500 nM.

The following assay can be used to evaluate the functional activity of compounds at 5HT7 receptors:

5-HT7 Receptor Mediated Adenylate Cyclase Activity:
Materials:
1.5 mL siliconized polypropylene microfuge tubes (Costar 3207)
12×75 mm boroscilicate glass tubes
Heated water bath
Glass-Teflon Homogenizer
Centrifuge
HEK-293 cells expressing 5-HT7 receptors
32P-ATP (30 Ci/mmol: NEG-003-New England Nuclear)
3H-cAMP (30 Ci/mmol: NET-275-New England Nuclear)

Methods:
Cells are grown according to standard cell culture techniques. Cells are harvested by replacing the media with phosphate-buffered saline containing 2.5 mM EDTA. The cells are homogenized using a hand-held glass-teflon homogenizer. The homogenate is centrifuged at 35,000×g for 10 minutes at 4 degrees C. The pellet is resuspended in 100 mM HEPES buffer containing 1 mM EGTA (pH 7.5) to a final protein concentration of 40 microgram protein per tube.

The "Reaction Mix" is prepared so that the following agents will be at these final concentrations in tube: 4.0 mM $MgCl_2$, 0.5 m MATP, 1.0 m McAMP, 0.5 mM IBMX, 10 mM, phosphocreatine, 0.31 mg/mL creatine phosphokinase, and 100 uM GTP0.5-1 microcuries a-[$^{32}$P]-ATP per tube.

Incubation is initiated by the addition of tissue to siliconized microfuge tubes (in triplicate). Incubation is at 37° C. for 15 minutes.

Each tube receives:
20 uL tissue, 20 uL drug or buffer (at 5× final concentration), 20 uL 100 nM agonist or buffer (at 5× final concentration), and 40 uL "Reaction Mix".

Incubation is terminated by the addition of 100 uL 2% SDS, 1.3 mM CAMP, 45 mM ATP solution containing 40,000 dpm [$^3$H]-cAMP to monitor the recovery of CAMP from the columns. The separation of [$^{32}$P]-ATP and [$^{32}$P]-cAMP is accomplished using the method of Salomon et al., *Analytical Biochemistry* 58: 541–548, 1974, which is incorporated herein by reference in its entirety. Radioactivity is quantified by liquid scintillation counting.

The maximal effect of agonists is defined in terms of the maximal effect of serotonin (5-HT). Antagonists are evaluated by their ability to inhibit 5HT-stimulated adenylate cyclase activity. $IC_{50}$ values are converted to apparent Ki values by the following equation: $IC_{50}/(1+([agonist]/EC_{50}$ of agonist)).

Activity of a combination of active compounds to produce an antidepressant effect and related pharmacological properties can be determined by methods (1)–(4) below, which are described in Koe, B. et al., *Journal of Pharmacology and Experimental Therapeutics*, 226 (3), 686–700 (1983), which is incorporated herein by reference in its entirety. Specifically, activity can be determined by studying (1) their ability to affect the efforts of mice to escape from a swim-tank (Porsolt mouse "behavior despair" test), (2) their ability to potentiate 5HT-induced behavioral symptoms in mice in vivo, (3) their ability to antagonize the serotonin-depleting activity of p-chloroamphetamine hydrochloride in rat brain in vivo, and (4) their ability to block the uptake of serotonin, norepinephrine and dopamine by synaptosomal rat brain cells in vitro. The ability of the active combination to counteract reserpine hypothermia in mice in vivo can be determined according to the methods described in U.S. Pat. No. 4,029,731, which is incorporated herein by reference in its entirety.

The following Examples illustrate the present invention. It is to be understood, however, that the invention, as fully described herein and as recited in the claims, is not intended to be limited by the details of the following Examples.

The following Examples illustrate the preparation of the compounds of the present invention. Melting points are uncorrected. NMR data are reported in parts per million and are referenced to the deuterium lock signal from the sample solvent (deuteriochloroform unless otherwise specified). Specific rotations were measured at room temperature using the sodium D line (589 nm). Commercial reagents were utilized without further purification. THF refers to tetrahydrofuran. DMF refers to N,N-dimethylformamide. Chromatography refers to column chromatography performed using 47–61 micron mesh silica gel and executed under nitrogen pressure (flash chromatography) conditions. Room or ambient temperature refers to 20–25° C. All non-aqueous reactions were run under a nitrogen atmosphere for convenience and to maximize yields. Concentration at reduced pressure means that a rotary evaporator was used.

EXAMPLES

Example 1

Step 1

8-Bromo-3-ethyl-quinoline

Enantiomeric (Both Enantiomers) and Racemic 3-Ethyl-8-Piperidin-3-yl-Quinoline

To a well-stirred mixture consisting of 2-bromo-aniline (5.4 g, 31.4 mmol), sodium 3-nitrobenzene sulfonate (4.25 g, 18.9 mmol), concentrated sulfuric acid (8.5 g, 177 mmol), and water (3.20 ml) heated to 100° C., 2-ethyl acrolein (5.0 ml, 51.06 mmol) was added. After maintaining the reaction temperature at 100° C. for 1 hour, the temperature was increased to 110° C. An additional portion of 2-ethyl acrolein (1.0 ml, 10.2 mmol) was added, and the reaction was stirred at 110° C. for 1 hour. The reaction temperature was then elevated to 120° C. prior to addition of another 1.0 ml (10.2 mmol) portion of 2-ethyl acrolein. After heating the reaction at 120 for 1 hour, the temperature was elevated to 130 prior to addition of 1.0 ml (10.2 mmol) of 2-ethyl acrolein. Finally, the reaction temperature was raised to 140° C. and maintained at that temperature for 2 hours following addition of a final portion (1.3 ml, 13.3 mmol) of 2-ethyl acrolein. The cooled reaction was quenched with ice (60 g), and the pH of the resulting mixture was adjusted to 14 by addition of 6 N aqueous sodium hydroxide. The reaction mixture was then extracted with three 100 ml portions of methylene chloride. The combined organic extracts were dried (anhydrous sodium sulfate) and concentrated in vacuo yielding an amber oil. Flash chromatography of the entire sample (silica gel, 47–61 micron mesh; elution with methylene chloride) afforded the title compound (3.70 g, 50% yield) as an amber oil.

MS m/z 236, 237, 238, 239 (M+1).

$^1$H NMR (400 MHz, CDCl$_3$) δ 8.9 (1H, m), 7.97 (1H, m), 7.91 (1H, m), 7.74 (1H, m), 7.36 (1H, m), 2.86 (2H, q, J=7.5 Hz), 1.34 (3H, t, J=7.5 Hz) ppm.

Step 2

3-Ethyl-8-pyridin-3-yl-quinoline

To a well-stirred mixture consisting of the title compound from the previous step (2.36 g, 10.0 mmol), diethyl (3-pyridyl) borane (1.67 g, 11.0 mmol), and bis (triphenylphosphine) palladium (II) chloride (913 mg, 1.3 mmol) in tetrahydrofuran (40 ml), an aqueous solution of sodium carbonate (4.24 g, 40 mmol in 20 ml water) is added, and the resulting reaction mixture is heated at reflux for 4 hours. Water (50 ml) was added to the well-stirred mixture. The aqueous phase of the biphasic reaction mixture is separated and extracted with three 50 ml portions of ethyl acetate. The solvent of the organic phase of the reaction mixture is removed in vacuo, and the residue is extracted with two 50 ml portions of ethyl acetate. The combined organic extracts are dried (anhydrous sodium sulfate) and concentrated in vacuo, yielding a viscous syrup. Flash chromatography of the entire sample (silica gel, 47–61 micron mesh; elution with ethyl acetate) yielded a pure portion of the title compound (830 mg, 35.4% yield) as a viscous amber syrup and a less pure (judged to be approximately 75% pure by NMR inspection) second portion of the title compound (700 mg), also an amber syrup.

MS m/z 234 (M+1).

$^1$H NMR (400 MHz, CDCl$_3$) δ 8.93 (1H, m), 8.80 (1H, m), 8.63 (1H, m), 8.10 (1H, m), 7.96 (1H, m), 7.81 (1H, m), 7.66 (1H, m), 7.60 (1H, m), 7.42 (1H, m), 2.84 (2H, q, J=7.5 Hz), 1.34 (3H, t, J=7.5 Hz) ppm.

Step 3

3-Ethyl-8-pyridin-3-yl-quinoline

To a solution of the title compound from the previous step (830 mg, 3.53 mmol) in anhydrous tetrahydrofuran (5.0 ml), 28.4 ml (28.4 mmol) of 1.0 M lithium triethylborohydride in tetrahydrofuran was added, and the resulting reaction mixture was stirred at ambient temperature for 18 hours. The reaction was quenched by cautious dropwise addition of water (50 ml). Solvents were removed in vacuo, affording a viscous oil which was extracted with three 25 ml portions of methylene chloride. The organic extract was dried (anhydrous sodium sulfate) and concentrated in vacuo to afford a viscous yellow syrup. The just-described procedure was repeated utilizing, respectively, 817 mg (3.49 mmol) and 27.9 ml (27.9 mmol) of the previous step title compound and 1.0 N triethylborohydride in tetrahydrofuran. The crude reaction products after work-up from both reactions (i.e., the viscous yellow syrups) were combined. Flash chromatography of the entire sample (silica gel, 47–61 micron mesh; elution with methylene chloride/methanol/concentrated aqueous ammonium hydroxide=90:9:1 in volume) afforded the title compound (480 mg) as a viscous yellow oil.

MS m/z 240 (M+1).

$^1$H NMR (400 MHz, CDCl$_3$) δ 8.78 (1H, m), 7.87 (1H, m), 7.58 (1H, m), 7.42–7.50 (2H, overlapping multiplets), 4.07 (1H, m), 3.32 (1H, m), 3.16 (1H, m), 2.80 (2H, q, J=7.5 Hz), 2.73–2.64 (2H, m), 2.2–2.0 (1H, m), 1.66–1.87 (3H, m), 1.32 (3H, t, J=7.5 Hz) ppm.

$^{13}$C NMR (125 MHz, CDCl$_3$) δ 150.9, 145.1, 143.3, 136.7, 134.1, 128.7, 126.6, 125.7, 125.3, 54.0, 47.1, 38.1, 31.6, 28.0, 26.4, 15.5 ppm.

Separation of the Enantiomers of the Racemic Title Compound

Step 4

Racemic 3-(3-Ethyl-quinolin-8-yl)-piperidine-1-carboxylic Acid Tert-Butyl Ester

To a well-stirred solution of the racemic title compound from the previous step (5.40 g, 23.9 mmol) in methylene chloride (50 ml) containing triethylamine (6.7 ml, 47.8 mmol), di-tert-butyl dicarbonate (7.80 g, 35.8 mmol) was added, and the resulting reaction mixture was stirred at ambient temperature for 5 hours. Saturated aqueous sodium bicarbonate (50 ml) was added with efficient stirring. The mixture was then extracted with two 20 ml portions of methylene chloride. The organic extracts were combined, washed with an equal volume of brine, dried (anhydrous sodium sulfate), and finally, concentrated in vacuo, affording a viscous syrup. Flash chromatography of the entire sample utilizing the Blotage Flash 401i™ silica gel flash chromatography module (silica gel 32–63 micron mesh prepacked cartridges supplied by the manufacturer: Biotage Division of the Dyax Corporation, Charlottesville, Va.), eluting with methylene chloride/methanol=99.5:0.5 in volume afforded the title compound (4.24 g, 52% yield) as a colorless solid.

MS m/z 340 (M+1).

$^1$H NMR (400 MHz, CDCl$_3$) δ 8.80 (1H, m), 7.88 (1H, m), 7.62 (1H, m), 7.50–7.43 (2H, overlapping multiplets), 4.32 (1H, m), 4.18 (1H, m), 4.10 (1H, m), 2.92 (1H, m), 2.85–2.76 (overlapping 1H, m and 2H, q centered at 2.80, J=7.5 Hz), 2.12 (1H, m), 1.82–1.71 (3H, m), 1.44 (s, 9H), 1.33 (3H, t, J=7.5 Hz) ppm.

Step 5

Enantiomeric 3-(3-Ethyl-quinolin-8-yl)-piperidine-1-carboxylic acid tert-butyl ester (both enantiomers)

Separation of the Enantiomers of the Step 4 Title Compound

Utilizing a Waters Prep LC 2000™ Preparative Chromatography System (Waters Chiracel™ OD 10 cmx 50 cm) preparative column; mobile phase: heptane/ethanol=98:2 in volume with 0.025% diethyl amine modifier; a flow rate of 225 ml/minute; 4.08 g of the title compound from the previous step dissolved in 10 ml of methylene chloride/methanol=4:1 in volume; injecting 204 mg of compound in the methylene chloride/methanol solution at a time; with approximate retention times for the enantiomers of 20 and 28 minutes) the enantiomers of the title compound from Step 4 above were isolated as yellow oils. Mass spectra and $^1$H NMR spectra of both enantiomers were identical in all respects to those of the Step 4 racemic compound. The entire 1.5 g sample of the more rapidly eluting enantiomer was further purified by flash chromatography utilizing the aforedescribed Blotage Flash 401i™ silica gel chromatography module (32–63 micron mesh factory packed cartridges; eluting with hexanes/ethyl acetate=8:2 in volume afforded 1.34 g of purified enantiomer as a colorless syrup.

MS m/z 340 (M+1).

$^1$H NMR (400 MHz, CDCl$_3$) δ

Step 6

Enantiomeric 3-Ethyl-8-piperidin-3-quinoline (Both Enantiomers)

Dissolution of either purified compound from the previous step with an ethyl acetate/hydrogen chloride saturated solution (0.25 ml of hydrogen chloride saturated ethyl acetate per 10 mg of tert-butyloxycarbonyl functionalized substrate; 4 hours reaction time at ambient temperature) yielded the corresponding deprotected enantiomer title compound of Step 5 as a mono-hydrochloric acid salt in quantitative yield. The free base of either enantiomeric title compound hydrochloric acid salt was obtained in quantitative yield as a colorless amorphous solid by dissolution of the salt form into a vigorously stirred (pH 10) aqueous sodium hydroxide/ethyl acetate biphasic mixture, separation and (anhydrous sodium sulfate drying) of the organic extract, followed by solvent removal in vacuo. The mass spectra and $^1$H NMR spectra of the enantiomeric free base compounds are identical in all respect to those of the previously described (Step 3 title compound) racemic counterpart.

Example 2

Enantiomeric (Both Enantiomers) and Racemic 3-Ethyl-7-Methyl-8-Piperidin-3-yl-Quinoline Step 1

3-(2-Methyl-6-nitro-phenyl)-pyridine

To a solution of 2-bromo-3-nitrotoluene 5.0 g (23 mmol) in tetrahydrofuran (180 ml); diethyl-3-pyridyl borane (3.89 g, 26 mmol), bis-triphenylphosphine palladium (II) chloride (2.42 g, 3.45 mmol), and a solution of sodium carbonate (12.19 g, 115 mmol) in water (60 ml) were sequentially added. The resulting well-stirred reaction mixture was then heated at 75° C. for 18 hours. The separated organic layer was diluted with ethyl acetate (200 ml) and extracted with an equal volume of water. The organic extract was then dried (anhydrous sodium sulfate) and concentrated in vacuo to afford a brown oil (9.4 g). Flash chromatography of the entire sample (silica gel, 47–61 micron mesh; elution with ethyl acetate/hexanes=1:1 in volume) afforded the title compound (2.40 g, 48% yield) as an amber oil.

$^1$HNMR (400 MHz, CDCl$_3$) δ 8.66 (m, 1H), 8.47 (m, 1H), 7.80 (m, 1H), 7.61 (m, 1H), 7.55 (m, 1H), 7.42 (m, 2H), 2.11 (s, 3H) ppm.

Step 2

3-Methyl-2-pyridin-3-yl-phenylamine

The title compound from the previous step (2.40 g, 12 mmol) dissolved in ethanol (50 ml) was hydrogenated (40 psi; 275 mg platinum oxide catalyst) for 3 hours. The catalyst was filtered and the solvent was removed in vacuo yielding an amber oil (1.4 g). Flash chromatography of the entire sample (silica gel, 41–67 micron mesh; elution with methylene chloride/methanol=96:4 in volume) afforded the title compound (1.40 g, 69% yield) as arm amber oil. TLC $R_f$ (silica gel plates; elution with methylene chloride/methanol=96:4 in volume; UV detection): 0.35.

$^1$HNMR (450 MHz, CDCl$_3$) δ 8.62 (m, 1H), 8.50 (m, 1H), 7.61 (m, 1H), 7.40 (m, 1H), 7.04 (m, 1H), 6.70 (m, 1H), 6.60 (m, 1H), 3.25 (br s, 2H), 2.00 (s, 3H) ppm.

Step 3

3-Ethyl-7-methyl-8-pyridin-3-yl-quinoline

A reaction mixture prepared by combining the title compound of the previous step (800 mg, 4.3 mmol), concentrated sulfuric acid (660 μl, 12 mmol), and sodium meta-nitrobenzene sulfonate (544 mg, 24 mmol) in water (450 μl) was well stirred and heated to 100° C. while 2-ethyl acrolein (1.26 ml, 13 mmol) was added dropwise over 4 minutes. The reaction mixture was heated at 100° C.; then at 120° C. for two hours. The reaction was then cooled to 100° C., and an additional 1.26 ml (13 mmol) of 2-ethyl acrolein was added dropwise over several minutes. After further heating at 120° C. for 2 hours, water (10 ml) was added and the solution was made basic (pH 12) with sodium hydroxide. The solution was then extracted with three 25 ml portions of methylene chloride. The combined organic extracts were dried (anhydrous sodium sulfate), and concentrated in vacuo to afford an oil (2.36 g). Flash chromatography of the entire sample (silica gel, 41–67 micron mesh; elution with methylene chloride/methanol=97:3 in volume) afforded the title compound as a colorless oil (567 mg, 53% yield). TLC $R_f$ (silica gel plates, elution with methylene chloride/methanol=97:3 in volume; UV detection): 0.31.

MS m/z 249 (M+1).

$^{13}$C NMR (125 MHz, CDCl$_3$) δ 152.0, 151.2, 148.1, 145.8, 138.4, 136.9, 135.7, 135.1, 133.4, 129.6, 127.4, 126.8, 123.2, 26.3, 21.2, 15.4 ppm.

Step 4

Racemic 3-Ethyl-7-methyl-8-piperidin-3-yl-quinoline

To a solution of the title compound from the previous step (567 mg, 2.3 mmol) in anhydrous tetrahydrofuran (20 ml), a solution of lithium triethylborohydride (1.0 M in anhydrous tetrahydrofuran; 8.1 ml, 8.1 mmol; Aldrich Chemical Company) was added dropwise over several minutes. After stirring at ambient temperature for 3 hours, an additional 4.05 ml (4.05 mmol) of 1.0 M triethylborohydride in anhydrous tetrahydrofuran was added dropwise. After 3 additional hours of stirring at ambient temperature, the reaction was quenched by dropwise addition of methanol. Saturated aqueous sodium carbonate was added, and the resulting mixture was extracted with three 25 ml portions of methylene chloride. The combined organic extracts were dried (anhydrous sodium sulfate) and concentrated in vacuo, yielding an oil (670 mg). Flash chromatography of the entire sample (silica gel, 47–61 micron mesh; elution with methylene chloride/methanol/concentrated aqueous ammonium hydroxide=79:20:1 in volume) afforded the title compound (87 mg, 15% yield) as a colorless oil.

TLC $R_f$ (silica gel plates; elution with methylene chloride/methanol/concentrated aqueous ammonium hydroxide=58.75:40:1.25 in volume; UV detection): 0.14.

MS m/z 255 (M+1).

$^1$H NMR (400 MHz, CDCl$_3$) δ 8.71 (m, 1H), 7.77 (m, 1H), 7.46 (m, 1H), 7.26 (m, 1H), 4.2 (m, 1H), 3.5 (m, 2H), 2.9 (m, 2H), 2.75 (q, 2H, J=7), 2.52 (s, 3H), 1.70 (m, 4H), 1.30 (t, 3H, J=7) ppm.

Step 5

Enantiomeric (Both Enantiomers)

Utilizing analogously the procedure of Step 4/Example 1, the racemic title compound of the previous step of this example was converted to the corresponding racemic nitrogen substituted tert-butoxycarbonyl compound, the separated/purified enantiomers of which were then isolated by the methodology of Step 5/Example 1. Finally, by the procedure of Step 6/Example 1, the enantiomers of the title compound of the previous step of this example were prepared in both mono-hydrochloride and free base form.

Example 3

Enantiomeric (Both Enantiomers) and Racemic 3,6-Dimethyl-8-Piperidin-3-yl-Quinoline Step 1

4-Methyl-2-pyridin-3-yl-phenylamine

To a mixture consisting of a tetrahydrofuran (125 ml) solution of 2-bromo-4-methylaniline (2.67 ml, 21 mmol), diethyl-3-pyridyl borane (3.08 g, 24 mmol), and bis(triphenylphosphine) palladium (II) chloride (2.21 g, 0.32 mmol), an aqueous solution sodium carbonate (11.13 g 10.5 mmol in 44 ml of water) was added. The well-stirred reaction mixture was heated at 75° C. for 18 hours. The upper layer of the cooled biphasic mixture was separated, dried (anhydrous sodium sulfate), and then filtered through celite. Solvent removal in vacuo yielded an oil (6.5 g). Flash chromatography of the entire sample (silica gel; elution with methylene chloride/methanol=95:5 in volume) afforded the title compound (1.85 g, 48% yield) as a colorless amorphous solid. TLC $R_f$ (silica gel plates; elution with methylene chloride/methanol=95:5; UV detection):0.53.

MS m/z 185 (M+1).

$^{13}$C NMR (125 MHz, CDCl$_3$) δ 150.2, 148.5, 141.5, 136.8, 135.6, 131.2, 130.1, 128.4, 124.0, 123.7, 116.3, 20.6 ppm.

Step 2

3,6-Dimethyl-8-pyridin-3-yl-quinoline

To a solid sample of the title compound from the previous step (1.85 g, 10 mmol) concentrated sulfuric acid (18 M, 27.5 mmol 1.52 ml) was slowly added, followed by addition of sodium meta-nitrobenzene sulfonate (1.26 g, 56 mmol) and water (1.05 ml). The well-stirred mixture was heated to 100° C. while 2-methyl acrolein (4.97 ml, 60 mmol) was added dropwise over 5 minutes. After stirring at 100° C. for ½ hour, the reaction temperature was elevated to 140° C. with continued stirring for 3 hours. After quenching with ice, the reaction mixture was made basic (pH 12) by addition of 50% aqueous sodium hydroxide. The mixture was then extracted with three 30 ml portions of methylene chloride. The combined organic extracts were dried (anhydrous sodium sulfate) and the solvent was removed in vacuo to afford an amber oil. Flash chromatography of the entire sample (silica gel; 41–67 micron mesh; elution with methylene chloride/methanol=96:4 in volume) afforded the title compound (650 mg, 28% yield) as an amorphous solid. TLC R$_f$ (silica gel plates; elution with methylene chloride/methanol=96:4 in volume; UV detection):0.24.

MS m/z 235 (M+1).

$^{13}$C NMR (125 MHz, CDCl$_3$) δ 151.8, 151.0, 148.4, 138.4, 136.7, 136.3, 135.5, 134.5, 131.7, 130.9, 130.1, 128.9, 126.9, 123.0, 21.8, 18.8 ppm.

Step 3

3.6-Dimethyl-8-piperidin-3-yl-quinoline

To a solution of the title compound from the previous step (650 mg, 28 mmol) in anhydrous tetrahydrofuran (20 ml), a 1.0 M solution of lithium triethylborohydride (9.70 ml, 9.7 mmol); Aldrich Chemical Co.) was added over several minutes. After stirring the reaction mixture for 2 hours at ambient temperature, an additional 2.8 ml (2.8 mmol) of 1.0 M lithium triethylborohydride in tetrahydrofuran was added; and ambient temperature stirring was continued for an additional 1 hour. The reaction was quenched by slow, cautious addition of methanol. Saturated aqueous sodium carbonate (15 ml) and methylene chloride were added, and the resulting mixture was extracted with three 25 ml portions of methylene chloride. The combined organic extracts were dried (anhydrous sodium sulfate) and concentrated in vacuo to afford an oil (600 mg). Flash chromatography of the entire sample (silica gel, 41–67 micron mesh; initial elution with methylene chloride/methanol/concentrated aqueous ammonia=84:15:1 in volume, followed by elution with methylene chloride/methanol/concentrated aqueous ammonia=73.75:25:1.25 in volume) afforded the title compound (100 mg, 15% yield) as a colorless oil. TLC R$_f$ (silica gel plates; elution with methylene chloride/methanol/concentrated aqueous ammonium hydroxide=82:15:1 in volume; UV detection):0.25.

MS m/z 241 (M+1).

$^{13}$C NMR (125 MHz, CDCl$_3$) δ 150.6, 143.3, 142.6, 136.2, 134.7, 130.4, 128.6, 127.7, 124.5, 53.6, 46.9, 37.8, 31.5, 27.7, 22.0, 18.8 ppm.

Step 4

Enantiomeric (Both Enantiomers)

Utilizing analogously the procedure of Step 4/Example 1, the racemic title compound of the previous step of this example was converted to the corresponding racemic nitrogen substituted tert-butoxycarbonyl compound, the separated/purified enantiomers of which were then isolated by the methodology of Step 5/Example 1. Finally, by the procedure of Step 6/Example 1, the enantiomers of the title compound of the previous step of this example were prepared in both mono-hydrochloride and free base form.

Example 4

Enantiomeric (Both Enantiomers) and Racemic 3.7-Dimethyl-8-Piperidin-3-yl-Quinoline Step 1

3-(2-Methyl-6-nitro-phenyl)-pyridine

To a mixture consisting of 2-bromo-3-nitrotoluene (5.0 g, 23 mmol) in tetrahydrofuran (180 ml), diethyl-3-pyridyl borane (3.89 g, 26 mmol), and bis (triphenylphosphine) palladium (II) chloride (2.42 g, 3.45 mmol), a solution of sodium carbonate (12.19 g, 115 mmol) in water was added. The well-stirred reaction mixture was heated at 75° C. for 18 hours. The organic and aqueous layers were separated, and the aqueous phase was extracted with ethyl acetate (100 ml). The combined organic extracts were dried (anhydrous sodium sulfate) and concentrated in vacuo to afford an oil (9.6 g). Flash chromatography of the entire sample (silica gel, 41–67 micron mesh; elution with ethyl acetate/hexanes= 1:1 in volume) afforded the title compound as a light yellow oil (1.87 g, 38% yield). TLC R$_f$ (silica gel plates; elution with ethyl acetate/hexanes=1:1 in volume; UV detection): 0.50.

MS m/z 215 (M+1).

$^{13}$C NMR (125 MHz, CDCl$_3$) δ 171.4, 148.1, 148.0, 139.6, 137.2, 134.7, 133.0, 131.7, 129.2, 123.9, 122.0, 21.0 ppm.

Step 2

3-Methyl-2-pyridin-3-yl-phenylamine

The title compound from the previous step (1.87 g, 8.7 mmol) dissolved in ethanol (40 ml) was hydrogenated (40 psi; 200 mg platinum oxide catalyst) for 4 hours. The catalyst was removed by filtration through celite. The filtrate was concentrated in vacuo to afford an amber oil (1.2 g). Flash chromatography of the entire sample (silica gel, 41–67 micron mesh; elution with methylene chloride/methanol= 96:4 in volume) afforded the title compound (1.17 g, 74% yield) as a tacky solid. TLC R$_f$ (silica gel plates; elution with methylene chloride/methanol=96:4 in volume; UV detection):0.38.

MS m/z 185 (M+1).

$^{13}$C NMR (125 MHz, CDCl$_3$) δ 151.1, 148.8, 144.4, 138.2, 137.4, 134.3, 129.1, 124.2, 123.8, 120.4, 113.3, 20.9 ppm.

Step 3

3.7-Dimethyl-8-pyridin-3-yl-quinoline

To a solid sample of the title compound from the previous step (1.17 g, 6.4 mmol), concentrated sulfuric acid (18 M, 17.6 mmol 980 μl) was slowly added, followed by addition of sodium meta-nitrobenzene sulfonate (800 mg, 3.6 mmol) and water (680 μl). The well-stirred mixture was heated at 100° C. while 2-methyl acrolein (1.59 ml, 19.2 mmol) was added dropwise over 5 minutes. After stirring at 100° C. for ½ hour, an addition 1.59 ml (19.2 mmol) portion of 2-methyl acrolein was added dropwise; and the well-stirred reaction mixture was then heated at 140° C. for 3 hours. Thin layer chromatography (TLC) inspection of a reaction aliquot revealed incomplete reaction. The reaction mixture temperature was lowered to 100° C., and a final 1.59 (19.2 mmol) portion of 2-methyl acrolein was added, with subsequent heating at 140° C. for 2 more hours to complete reaction. The reaction mixture was poured into ice (50 g) made basic (pH 10) by addition of 50% aqueous sodium hydroxide, and then extracted with three 50 ml portions of methylene chloride. The combined organic extracts were dried (anhydrous sodium sulfate) and concentrated in vacuo to afford an oil (3.2 g). Flash chromatography of the entire sample (silica gel, 47–61 micron mesh; elution with methylene chloride/methanol=96:4 in volume) afforded the title compound (328 mg, 22% yield) as an amber oil. TLC R$_f$ (silica gel plates; elution with methylene chloride/methanol 96:4 in volume, UV detection):0.34.

$^1$H NMR (400 MHz, CDCl$_3$) δ 8.6 (m, 3H), 7.88 (m, 1H), 7.64 (m, 2H), 7.40 (m, 2H), 2.42 (s, 3H), 2.38 (s, 3H) ppm.

Step 4

Racemic 3,7-Dimethyl-8-piperidin-3-yl-quinoline

To a solution of the title compound from the previous step (328 mg, 1.4 mmol) in anhydrous tetrahydrofuran (10 ml), a 1.0M solution of lithium triethylborohydride in tetrahydrofuran (4.90 ml, 4.9 mmol) was added dropwise. The reaction mixture was stirred at ambient temperature for 3 hours. After dropwise addition of a second portion of 1.0 M lithium triethylborohydride in tetrahydrofuran (1.40 ml, 1.4 mmol), ambient temperature stirring was continued for an additional 1.5 hours. The reaction was quenched by cautious dropwise addition of methanol (1 ml). Saturated aqueous sodium carbonate and methylene chloride were added to the well-stirred mixture, which was then extracted with three 30 ml portions of methylene chloride. The combined organic extracts were dried (anhydrous sodium sulfate) and concentrated in vacuo to afford a yellow oil (470 mg). Flash chromatography of the entire sample (silica gel, 47–41 micron mesh; initial elution with methylene chloride/methanol/concentrated aqueous ammonium hydroxide=84:15:1 in volume, followed by elution with methylene chloride/methanol/concentrated aqueous ammonium hydroxide=59:40:1 in volume) afforded the title compound (45 mg, 13% yield) as an amorphous foam. TLC $R_f$ (silica gel plates; elution with methylene chloride/methanol/concentrated aqueous ammonium hydroxide=84:15:1 in volume, UV detection):0.28.

MS m/z 241 (M+1).

$^1$H NMR (400 MHz, CDCl$_3$) δ 8.65 (m, 1H), 7.76 (m, 1H), 7.45 (m, 1H), 7.26 (m, 1H), 4:32 m, 1H), 3.22 (m, 1H), 3.08 (m, 1H), 2.92 (m, 2H), 2.75 (s, 3H), 2.42 (m, 4H), 1.80 (m, 3H) ppm.

Step 5

Enantiomeric (Both Enantiomers)

Utilizing analogously the procedure of Step 4/Example 1, the racemic title compound of the previous step of this example was converted to the corresponding racemic nitrogen substituted tert-butoxycarbonyl compound, the separated/purified enantiomers of which were then isolated by the methodology of Step 5/Example 1. Finally, by the procedure of Step 6/Example 1, the enantiomers of the title compound of the previous step of this example were prepared in both mono-hydrochloride and free base form.

Example 5

Enantiomeric (Both Enantiomers) and Racemic 3.5-Dimethyl-8-Piperidin-3-yl-Quinoline

Step 1

3-(4-Methyl-2-nitro-phenyl)-pyridine

To a well-stirred mixture consisting of 4-bromo-3-nitrotoluene (4.0 g, 18.5 mmol) in tetrahydrofuran (145 ml), diethyl-3-pyridylborane (3.12 g, 21 mmol), and bis (triphenylphosphine) palladium (II) chloride (1.94 g, 2.8 mmol), a solution of sodium carbonate (9.8 g, 92.5 mmol) in water (50 ml) was added. The reaction mixture was heated to 75° C. for 18 hours. The organic layer of the biphasic mixture was dried (anhydrous sodium sulfate), and the solvent was removed in vacuo to afford an oil (7.0 g). Flash chromatography of the entire sample (silica gel, 47–61 micron mesh; elution with ethyl acetate/hexanes=1:1 in volume) afforded the title compound (2.58 g, 65% yield) as a light yellow foam. TLC $R_f$ (silica get plates; elution with ethyl acetate/hexanes=1:1 in volume, UV detection):0.51.

MS m/z215 (M+1).

$^{13}$C NMR (125 MHz, CDCl$_3$) δ 148.4, 147.9, 140.3, 136.4, 134.3, 133.9, 132.1, 130.1, 125.2, 123.6, 21.1 ppm.

Step 2

5-Methyl-2-pyridin-3-yl-phenylamine

The title compound from the previous step (2.58 g, 12 mmol) dissolved in ethanol (65 ml) was hydrogenated (40 psi; 275 mg platinum oxide catalyst) for 3 hours. The catalyst was removed by filtration through celite, and the filtrate was concentrated in vacuo to afford an amber oil (2.27 g). Flash chromatography of the entire sample (silica gel, 47–61 micron mesh; elution with methylene chloride/methanol=95:5 in volume) afforded the title compound (1.6 g, 73% yield) as a yellow oil. TLC $R_f$ (silica gel plates; elution with methylene chloride/methanol=95:5 in volume, UV detection):0.59.

MS m/z 185 (M+1).

$^{13}$C NMR (125 MHz, CDCl$_3$) δ 150.2, 148.2, 143.8, 139.7, 135.6, 130.7, 123.8, 121.2, 120.2, 116.7, 21.4 ppm.

Step 3

3.5-Dimethyl-8-pyridin-3-yl-quinoline

To a solid sample of the title compound from the previous step (1.60 g, 8.7 mmol), concentrated sulfuric acid (18 M, 1.32 ml, 23.9 mmol) was slowly added, followed by addition of sodium meta-nitrobenzene sulfonate (1.10 g, 4.9 mmol) and water (1.0 ml). The well-stirred mixture was heated at 100° C. while 2-methyl acrolein (4.31 ml, 52 mmol) was added dropwise over a 5 minute period. After 112 hour heating at 100° C., the reaction was heated for 6 hours at 140° C. The mixture was diluted with water (50 ml) and the pH was adjusted to 10 with 50% aqueous sodium hydroxide. Three successive extractions were made with 40 ml portions of methylene chloride. The combined organic extracts were dried (anhydrous sodium sulfate) and concentrated in vacuo to afford an oil 1.06 g. Flash chromatography of the entire sample (silica gel, 47–61 micron mesh; elution with methylene chloride/methanol=97:3 in volume) afforded the title compound as a colorless oil (220 mg, 10.8% yield). TLC $R_f$ (silica gel plates; elution with methylene chloride/methanol=97:3 in volume, UV detection):0.20.

MS m/z 235 (M+1).

Step 4

Racemic 3.5-Dimethyl-8-piperidin-3-yl-quinoline

To a well-stirred solution of the title compound from the previous step (220 mg, 0.94 mmol) in tetrahydrofuran (7.5 ml), a 1.0 M solution of lithium triethylborohydride in tetrahydrofuran (3.30 ml, 3.3 mmol) was added dropwise over several minutes. The reaction was stirred at ambient temperature for 4 hours, and quenched by cautious dropwise addition of methanol. Methylene chloride (25 ml) and aqueous sodium carbonate (25 ml) were added to the well-stirred mixture, which was then extracted with two 30 ml portions of methylene chloride. The combined organic extracts were dried (anhydrous sodium sulfate) and concentrated in vacuo to afford an orange oil (440 mg). Flash chromatography of the entire sample (silica gel, initial elution with methylene chloride/methanol/concentrated aqueous ammonium hydroxide=84:15:1 in volume followed by elution with methylene chloride/methanol/concentrated aqueous ammonium hydroxide=73.75:25:1.25 in volume) afforded the title compound (17 mg, 7.5% yield) as a colorless oil. TLC $R_f$ (silica gel plates; elution with methylene chloride/methanol/concentrated aqueous ammonium hydroxide=73.75:25:1.25 in volume, UV detection):0.33.

MS m/z 241 (M+1).

$^{13}$C NMR (125 MHz, CDCl$_3$) δ 150.9, 144.8, 140.8, 132.1, 131.8, 130.0, 127.7, 127.0, 125.0, 53.4, 46.7, 37.7, 31.3, 27.4, 19.1, 18.8 ppm.

Step 5

Enantiomeric (Both Enantiomers)

Utilizing analogously the procedure of Step 4/Example 1, the racemic title compound of the previous step of this example was converted to the corresponding racemic nitrogen substituted tert-butoxycarbonyl compound, the separated/purified enantiomers of which were then isolated by the methodology of Step 5/Example 1. Finally, by the procedure of Step 6/Example 1, the enantiomers of the title compound of the previous step of this example were prepared in both mono-hydrochloride and free base form.

EXAMPLE 6

Enantiomeric (Both Enantiomers) and Racemic 6-Chloro-3-Methyl-8-Piperidin-3-yl-Quinoline Step 1

6-Chloro-3-methyl-8-pyridin-3-yl-quinoline

To a well-stirred mixture consisting of 2-bromo-4-chloroaniline (5.0 g, 24 mmol) in tetrahydrofuran (180 ml), diethyl-3-pyridyl borane (4.07 g, 28 mmol), and bis(triphenylphosphine) palladium (II) chloride (2.53 g, 3.6 mmol), a solution of sodium carbonate (12.72 g, 120 mmol) in water (60 ml) was added. The reaction was then heated at 75° C. for 18 hours. The layers of the biphasic mixture were separated, and the aqueous phase was extracted with an equal volume of ethyl acetate. The combined original reaction organic phase and ethyl acetate extract were dried and concentrated in vacuo to afford an oil (9.4 g). Flash chromatography of the entire sample (silica gel; initial elution with ethyl acetate/hexanes=8:2 in volume followed by elution with pure hexane) afforded the title compound as a colorless oil (3.64 g, 74% yield). TLC $R_f$ (silica gel plates; elution with ethyl acetate, UV detection):0.46.

Step 2

6-Chloro-3-methyl-8-piperidin-3-yl-quinoline

To a well-stirred mixture consisting of the title compound from the previous step (3.64 g, 17.8 mmol), sodium 3-nitrobenzene sulfonate (2.33 g, 10 mmol), and water (1.79 ml), 2.72 ml (49 mmol) of concentrated sulfuric acid (18 M) was cautiously added. The reaction mixture was heated to 100° C., and 2-methyl acrolein (4.39 ml, 53 mol) was added. The reaction was stirred at 100° C. for 20 minutes, and then stirred at 140° C. for 2 hours. After lowering the reaction temperature back to 100° C., another 4.39 ml (53 mmol) portion of 2-methyl acrolein was added dropwise. The reaction temperature was again elevated to 140° C. and maintained at that temperature for 1.5 hours. An equal volume of ice was used to quench the reaction; and the resulting mixture was made basic (pH=12) by addition of 50% aqueous sodium hydroxide. The mixture was then extracted with 75 ml of methylene chloride. The organic extract was dried (anhydrous sodium sulfate) and concentrated in vacuo, yielding a dark oil. Flash chromatography of the entire sample (silica gel, 47–61 micron mesh; elution with initially ethyl acetate/hexanes=8:2 in volume, steadily increasing the polarity of the eluting solvent, finally to pure ethyl acetate) afforded the title compound as a colorless oil (343 mg, 7.6% yield). TLC $R_f$ (silica gel plates; elution with ethyl acetate/hexanes=8:2 in volume, UV detection):0.35.

MS m/z 255 (M+1).

Step 3

Racemic 6-Chloro-3-methyl-8-piperidin-3-yl-quinoline

To a well-stirred solution of the title compound of the previous step (150 mg, 0.59 mmol) in anhydrous tetrahydrofuran (5 ml) a 1.0 M solution of lithium triethylborohydride in tetrahydrofuran (2.1 ml, 2.1 mmol) was added, and the resulting reaction mixture was stirred at ambient temperature for 4 hours, prior to quenching by cautious addition of 200 μl of methanol. Saturated aqueous sodium carbonate (10 ml) and methylene chloride were added, with vigorous stirring. The mixture was then extracted with three 15 ml portions of methylene chloride. The combined organic extracts were dried (anhydrous sodium sulfate) and concentrated in vacuo, yielding a (230 mg) yellow oil. Flash chromatography of the entire sample (silica gel, 47–61 micron mesh; elution with initially methylene chloride/methanol/concentrated aqueous ammonium hydroxide=97.25:2.50:0.25 in volume, steadily increasing the polarity of the eluting system to a final methylene chloride/methanol/concentrated aqueous ammonium hydroxide=89:10:1 in volume) afforded the title compound (17 mg, 11% yield) as a colorless oil. TLC $R_f$ (silica gel plates; elution with methylene chloride/methanol/aqueous concentrated ammonium hydroxide=89:10:1 in volume. UV detection):0.39.

MS m/z 261 (M+1).

$^{13}$C NMR (175 MHz, CDCl$_3$) δ 151.6, 145.4, 143.2, 134.4, 132.4, 131.6, 129.2, 126.4, 124.1, 53.5, 46.8, 37.9, 31.3, 27.5, 18.8 ppm.

Step 4

Enantiomeric (Both Enantiomers)

Utilizing analogously the procedure of Step 4/Example 1, the racemic title compound of the previous step of this example was converted to the corresponding racemic nitrogen substituted tert-butoxycarbonyl compound, the separated/purified enantiomers of which were then isolated by the methodology of Step 5/Example 1. Finally, by the procedure of Step 6/Example 1, the enantiomers of the title compound of the previous step of this example were prepared in both mono-hydrochloride and free base form.

Example 7

Enantiomeric (Both Enantiomers) and Racemic 4-Methyl-8-Piperidin-3-yl-Quinoline

Step 1

3-(2-Nitro-phenyl)-pyridine

To a mixture consisting of 1-bromo-2-nitrobenzene (2.12 g, 8.7 mmol), diethyl (3-pyridyl) borane (1.47 g, 10.0 mmol), and bis (triphenylphosphine) palladium (II) chloride (913 mg, 1.3 mmol) in tetrahydrofuran (40 ml), sodium carbonate (4.24 g, 40.0 mmol) was added, and the resulting reaction mixture was heated at reflux for 4 hours. Water (40 ml) was added to the cooled reaction mixture which was then extracted with three 25 ml portions of ethyl acetate. The combined organic extracts were dried (anhydrous sodium sulfate) and concentrated in vacuo to afford a tacky residue. Flash chromatography of the entire sample (silica gel, 47–61 micron mesh; elution initially with methylene chloride and finally with methylene chloride/methanol=98:2 in volume) afforded the title compound as a viscous amber oil (713 mg, 41% yield). Subsequent eluent contained less pure product which was further purified by a similar flash chromatography, eluting with methylene chloride/methanol=99:1 in volume, thus affording an additional 488 mg (28% yield) of the purified title compound, again as a viscous amber oil.

MS m/z 200 (M+1).

$^1$H NMR (400 MHz, CDCl$_3$) δ 8.65 (1H, M), 8.58 (1H, m), 7.99 (1H, m), 7.60–7.73 (2H, overlapping multiplets), 7.56 (1H, m), 7.43 (1H, m), 7.36 (1H, m) ppm.

Step 2

2-Pyridin-3-yl-phenylamine

A solution of the title compound from the previous step (16.3 g, 81 mmol) in methanol (300 ml) was hydrogenated (50 psi; 1.65 g of platinum oxide catalyst) for 3.5 hours. The catalyst was filtered, and the filtrate was concentrated in vacuo to afford a viscous amber oil. Flash chromatography of the entire sample (silica gel, 47–61 micron mesh; elution with ethyl acetate) afforded the title compound 13.5 g, (94.6% yield) as an amber oil.

MS m/z 171 (M+1).

$^1$H NMR (400 MHz, CDCl$_3$) δ 8.71 (1H, m), 8.58 (1H, m), 7.80 (1H, m), 7.37 (1H, m), 7.19 (1H, m), 7.10 (1H, m), 6.84 (1H, m), 6.78 (1H, m), 3.70 (2H, broad s) ppm.

Step 3

Racemic 2-Piperidin-3-yl-phenylamine

To a well-stirred solution of the title compound from the previous step (1.83 g, 10.8 mmol) in tetrahydrofuran (5.0 ml), 37.8 ml (37.8 mmol) of 1M lithium triethylborohydride in tetrahydrofuran was added dropwise over a 15 minute period. The reaction mixture was then stirred at ambient temperature for 18 hours. The reaction was then quenched by cautious dropwise addition of water (100 ml). Solvents were removed in vacuo, yielding a viscous oil. Flash chromatography of the entire sample (silica gel, 47–61 micron mesh; elution with methylene chloride/methanol/concentrated aqueous ammonium hydroxide=90:9:1 in volume) afforded (after appropriate combining of chromatography column fractions of similar purity as per thin layer chromatography inspection) a 470 mg viscous syrup sample (which solidified on standing, shown to be predominantly title compound product by NMR inspection) and a considerably less pure sample of the desire product (600 mg, a viscous oil). Trituration of the 470 mg sample with methylene chloride (2 ml) afforded a 100 mg sample of the title compound (a colorless amorphous solid, isolated by suction filtration; no detectable impurities by NMR inspection). A second flash chromatography of the entire aforedescribed 600 mg impure sample (same chromatography conditions) yielded an additional 160 mg of the purified title compound product (colorless amorphous solid; 260 mg, 14% yield).

MS m/z 177 (M+1).

$^1$H NMR (400 MHz, CDCl$_3$) δ 9.40 (1H, m), 9.33 (1H, m), 9.10 (1H, m), 9.05 (1H, M), 5.60 (2H, m), 5.0–5.34 (3H, overlapping multiplets), 4.30 (2H, m), 4.12 (2H, m) ppm.

Step 4

Racemic 4-Methyl-8-piperidin-3-yl-quinoline

To a well-stirred slurry of the title compound from the previous step (254 mg, 1.49 mmol) in ethanol, 0.12 ml of 12 N hydrochloric acid was added, affording a clear solution. Ferric chloride hexahydrate (557 mg, 2.06 mmol) and zinc chloride (24 mg, 10.18 mmol) were added, and the reaction mixture was heated to 60° C. Methyl vinyl ketone (0.016 ml, 0.19 mmol) was added, and the reaction temperature was maintained at 60° C. for 1 hour, during which time, additional 0.016 ml portions of methyl vinyl ketone were added at 10 minute intervals. The reaction was then refluxed for 2 hours. Volatiles were removed in vacuo, yielded a viscous syrup. The residual syrup was made basic by thorough trituration with 10 ml of 3 N aqueous sodium hydroxide. The resulting mixture was extracted with three 10 ml portions of methylene chloride. The combined organic extracts were, in turn, extracted with an equal volume of brine, dried (anhydrous sodium sulfate), and concentrated in vacuo, yielding a viscous oil. Several repetitive flash chromatography procedures utilizing the entire crude product sample (silica gel, 47–61 micron mesh; eluting in the initial procedure with methylene chloride/methanol=98:2 in volume, and in the repeated chromatography with 100% methylene chloride) yielded the purified product as a colorless oil (131 mg, 39% yield).

MS m/z 227 (M+1).

$^1$H NMR (400 MHz, CDCl$_3$) δ 8.76 (1H, m), 7.85 (1H, m), 7.58–7.48 (2H, overlapping multiplets), 7.22 (1H, m), 4.14 (1H, m), 3.34 (1H, m), 3.19 (1H, m), 2.68 (3H, s), 2.60–2.80 (2H, m), 2.1 (1H, m), 1.90–1.6 (3H, m) ppm.

Separation of Enantiomers of the Title Compound

Step 5

Racemic 3-(4-Methyl-quinolin-8-yl-piperidine-1-carboxylic Acid Tert-Butyl Ester

Utilizing the method of Example 1, Step 6, the entire 131 mg (0.58 mmol) of the racemic free base title compound from the previous step was converted into the corresponding N-tert-butyloxycarbonyl functionalized title compound of this step (yielding 120 mg, 63.4% yield, as a colorless oil).

MS m/z (M+1).

$^1$H NMR (400 MHz, CDCl$_3$) δ 8.78 (1H, m), 7.87 (1H, m), 7.46–7.60 (2H, overlapping multiplets), 7.23 (1H, m), 4.34 (1H, m), 4.20 (1H, m), 4.15 (1H, m), 2.91 (1H, m), 2.81 (1H, m), 2.67 (3H, s), 2.12 (1H, m), 1.76 (3H, m), 1.44 (9H, s) ppm.

Enantiomeric 3-(4-Methyl-quinolin-8-yl)-piperidine-1-carboxylic Acid Tert-Butyl Ester (Both Enantiomers)

Step 6

Separation of the Enantiomers of the Step 5 Title Compound

Utilizing the Waters Prep LC2000™ Preparative Chromatography System described in Example 1 (Chiracal™ OD 2.1 cm×25 cm preparative column; mobile phase: heptane/ethanol=98:2 in volume with 0.025% diethyl amine as modifier; a flow rate of 10 ml/minute; 134 mg of the title compound from the previous step dissolved in methylene chloride/methanol/mobile phase solution=1:1:1 in volume; injecting 10 mg of dissolved compound at a time; with approximate retention times of 25 and 35 minutes) the enantiomers of the title compound from Step 5 above were isolated as colorless oils (31 mg of the foster eluting enantiomer and 17 mg of the slower eluting enantiomer were obtained). The $^1$H NMR spectra of both enantiomers were identical in all respects to that of the racemic title compound of Step 5, this example.

Step 7

Enantiomeric 4-Methyl-8-piperidin-3-yl-quinoline (Both Enantiomers)

The entire 31 mg and 17 mg samples respectively of the faster and slower eluting enantiomeric title compounds prepared in the previous step were dissolved in 0.5 ml of chloroform. A hydrogen chloride saturated diethyl ether solution (1 ml) was added to each. Both reaction mixtures were stirred for 18 hours at ambient temperature. Solvent removal in vacuo afforded 15 mg and 9.5 mg respectively of the title compound enantiomers derived from the faster and slower elution Step 6 enantiomeric compounds as colorless amorphous solids. NMR obtained with mono-hydrochloride salt of more rapidly eluted enantiomer:

$^1$H NMR (400 MHz, CDCl$_3$) δ 9.09 (1H, m), 8.46 (1H, m), 8.18 (1H, m), 7.96–8.09 (2H, overlapping multiplets), 4.21 (1H, m), 3.65 (1H, m), 3.57 (1H, m), 3.46 (1H, m), 3.18 (1H, m), 3.07 (3H, s), 2.08–2.33 (3H, m), 1.93–2.05 (1H, m) ppm.

Example 8

Enantiomeric (Both Enantiomers) and Racemic 3-Methyl-8-Piperidin-3-yl-Quinoline

Step 1

3-Methyl-8-pyridin-3-yl-quinoline

A well-stirred mixture consisting of Example 7, Step 2 (3.20 g, 18.8 mmol), 2.51 g (11.1 mmol) of sodium 3-nitrobenzene sulfonate, 5.1 g (51.9 mmol) of concentrated sulfuric acid, and water (1.89 ml) was heated to 100° C. 2-Methyl acrolein (1.0 ml, 12.1 mmol) was added, and the reaction temperature was maintained at 100° C. for 1 hour. The reaction temperature was then elevated to 110° C., an additional 1 ml (12.1 mmol) portion of 2-methyl acrolein was added, and the 110° C. reaction temperature was maintained for 1 hour. Subsequently, the above described sequence of elevating the reaction temperature by 10° C. increments, followed by an addition of 1.0 ml of 2-methyl acrolein and an hour of heating at the newly established temperature was repeated three more times (with reaction temperatures of 120° C., 130° C., and finally, 140° C.). The reaction temperature was then lowered to and maintained at 90° C., affording an acidic aqueous phase and a pliable tacky gum. The acidic layer was carefully siphoned off, and the residual gum was thoroughly triturated/pulped with several 25 ml portions of 1 N hydrochloric acid. The combined acidic aqueous extracts were made basic (pH=14) by addition of 50% aqueous sodium hydroxide and, in turn, extracted with two 50 ml portions of methylene chloride. The organic extract was dried (anhydrous sodium sulfate) and concentrated in vacuo to afford an amber syrup. Flash chromatography of the entire sample (silica gel, 47-61 micron mesh; elution with ethyl acetate) yielded the title compound (790 mg, 19.1% yield) as a viscous colorless syrup.

MS m/z 221 (M+1).

$^1$H NMR (400 MHz, CDCl$_3$) δ 8.91 (1H, m), 8.77 (1H, m), 8.63 (1H, m), 8.07 (1H, m), 7.97 (1H, m), 7.66 (1H, m), 7.60 (1H, m), 7.40 (1H, m), 2.52 (3H, s) ppm.

Step 2

Racemic 3-Methyl-piperidin-3-yl-quinoline

To a solution of the title compound from the previous step (590 mg, 2.68 mmol) in tetrahydrofuran (8.0 ml), a 1 M solution of lithium triethylborohydride in tetrahydrofuran (10.72 ml, 10.72 mmol) was added, and the reaction was stirred at ambient temperature for 7 hours. An additional 5.36 ml (5.36 mmol) portion of 1 M lithium triethylborohydride in tetrahydrofuran was added, and the reaction mixture was stirred at ambient temperature for 18 hours prior to quenching by cautious dropwise addition of water (50 ml). Solvents were then removed in vacuo, and the residue was extracted with three 20 ml portions of methylene chloride. The organic extract was dried (anhydrous sodium sulfate) and concentrated in vacuo, affording an amber oil. Flash chromatography of the entire sample (silica gel, 47–61 micron mesh; elution with methylene chloride/methanol/concentrated aqueous ammonium hydroxide= 90:9:1 in volume) yielded the title compound (302=mg, 49.8% yield) as a light orange foam.

MS m/z 227 (M+1).

$^1$H NMR (400 MHz, CDCl$_3$) δ 8.76 (1H, m), 7.88 (1H, m), 7.58 (1H, m), 7.40–7.54 (2H, overlapping multiplets), 4.09 (1H, m), 3.33 (1H, m), 3.17 (1H, M), 2.60–2.80 (2H, m), 2.50 (3H, s), 2.09 (1H, m), 1.58–1.93 (3H, m) ppm.

Separation of the Enantiomers of the Racemic Title Compound

Step 3

Enantiomeric 3-(3-Methyl-quinolin-8-yl-piperidine-1-carboxylic Acid Tert-Butyl Ester To a well-stirred solution of the racemic title compound from the previous step (302 mg, 1.33 mmol) in methylene chloride (20 ml) containing 0.56 ml (4.0 mmol) of triethylamine, 436 mg (2.0 mmol) of di-tert-butyl dicarbonate was added, and the resulting reaction mixture was stirred for 48 hours at ambient temperature. Aqueous saturated sodium bicarbonate (20 ml) was added with efficient stirring. The mixture was then extracted with two 20 ml portions of methylene chloride. The combined organic extracts were, in turn, extracted with an equal volume of brine, dried (anhydrous sodium sulfate), and finally, concentrated in vacuo, affording a viscous syrup. Flash chromatography of the entire sample (silica gel, 47–61 micron mesh; elution with methylene chloride/methanol=99:1 in volume) affording the title compound as a colorless oil.

MS m/z 326 (M+1).

$^1$H NMR (400 MHz, CDCl$_3$) δ 8.77 (1H, m), 7.87 (1H, m), 7.40–750 (2H, overlapping multiplets), 7.60 (1H, m), 4.34 (1H, m), 4.21 (1H, m), 4.09 (1H, m), 2.92 (1H, m), 2.80 (1H, m), 2.50 (3H, s), 2.20 (1H, m), 1.78 (3H, m), 1.44 (9H, s) ppm.

Step 4

Separation of the Enantiomers of the Step 2 Title Compound

Utilizing the Waters Prep LC2000™ Preparative Chromatography System described in Example 1 (Chiracal™ OD 10 cm×50 cm preparative column; mobile phase: hexanes/ ethanol=98:2 in volume with 0.025% diethyl amine as modifier; a flow rate of 225 ml/minute; 247 mg of the racemic title compound from the previous step dissolved in methylene chloride/methanol=1:1 in volume; injecting the entire 247 mg sample of dissolved compound as a single load; with approximate retention times of 25 and 40 minutes) the enantiomers were separated. The process yielded 119 mg of the faster eluting enantiomer. The $^1$N HMR spectra for the enantiomers are identical to those obtained with the racemic title compound of Step 3, above.

Step 5

Enantiomeric 3-Methyl-8-piperidin-3-yl-quinoline (Both Enantiomers)

A 90 mg sample of the faster eluting title compound enantiomer isolated in the previous step was dissolved in 1 ml of methanol. A saturated hydrogen chloride solution in diethyl ether was added, and the reaction mixture was stirred at ambient temperature for 18 hours. Solvents and excess hydrochloric acid were removed in vacuo, affording a colorless glass. Trituration with ethyl acetate (10 ml) yielded the enantiomeric title compound as an amorphous solid mono-hydrochloride salt (61 mg).

Mono-hydrochloride salt:

$^1$H NMR (400 MHz, CDCl$_3$) δ 9.15 (1H, m), 9.09 (1H, m), 8.21 (1H, m), 8.12 (1H, m), 7.96 (1H, m), 4.24 (1H, m), 3.66 (1H, m), 3.57 (1H, m), 3.46 (1H, m), 3.20 (1H, m), 2.75 (3H, s), 2.08–2.34 (3H, m), 1.90–2.08 (1H, m) ppm.

The free base of the enantiomeric title compounds of this step was prepared by the method of Example 1, Step 6. The mass spectra and $^1$H NMR spectra of the enantiomeric title compound free bases are identical in all respects to the racemic title compound free base of Step 2, this Example.

Example 9

Enantiomeric (Both Enantiomers) and Racemic 3-ethyl-8-Pyrrolidin-3-yl-Quinoline

Step 1

3-(3-Ethyl-quinolin-8-yl)-3-hydroxy-pyrrolidine-1-carboxylic Acid Tert-Butyl Ester To a well-stirred solution of the title compound of Example 1, Step 1 (2.10 g, 8.9 mmol) in 30 ml of anhydrous tetrahydrofuran chilled to and maintained at −77° C., a 2.5 M solution of n-butyl lithium in hexanes (3.60 ml, 8.9 mmol; Aldrich Chemical Co.) is added dropwise over a 10 minute period. The reaction was stirred at −77° C. for 15 minutes before adding a solution of 3-oxo-pyrrolidine-1-carboxylic acid tert-butyl ester (1.65 g, 8.9 mmol) in anhydrous tetrahydrofuran (10 ml). The reaction mixture was allowed to warm to ambient temperature and stir at that temperature for 3 hours before quenching by cautious dropwise addition (with cooling) of saturated aqueous sodium bicarbonate (50 ml total). The resulting mixture was thoroughly extracted with three 20 ml of ethyl acetate. The combined organic extracts were, in turn, extracted with an equal volume portion of brine, dried (anhydrous sodium sulfate) and, finally, concentrated in vacuo, yielding a viscous syrup. Flash chromatography of the entire sample (silica gel, 47–61 micron mesh; elution with methylene chloride/methanol=98:2 in volume) afforded the title compound (352 mg, 11.5% yield) as a viscous yellow oil.

MS m/z 343 (M+1).

$^1$H NMR (400 MHz, CDCl$_3$) δ 8.70 (1H, m), 7.96 (1H, m), 7.70 (1H, m), 7.53 (1H, m), 7.44 (1H, m), 4.14 (1H, m), 3.93 (1H, m), 3.60–3.76 (2H, m), 3.48–3.60 (1H, m), 2.83 (2H, m), 2.42 (2H, m), 1.45 and 1.43 (9H, two singlets), 1.34 (3H, m) ppm.

Step 2

8-(2.5-Dihydro-1H-pyrrol-3-yl)-3-ethyl-quinoline

The title compound from the previous step (350 mg, 1.02 mmol) was dissolved in concentrated sulfuric acid. The solution was heated at 100° C. for 6 hours, and then stirred at ambient temperature for 48 hours. The reaction mixture was chilled to ice bath temperature, cautiously diluted with water (dropwise addition, 25 ml), and the made basic (pH=14) by addition of 50% aqueous sodium hydroxide. The mixture was then extracted with two 20 ml portions of methylene chloride. The combined organic extracts were, in turn, extracted with an equal volume portions of water and then brine, dried (anhydrous sodium sulfate), and concentrated in vacuo, yielding a viscous syrup. Flash chromatography of the entire sample (silica gel, 47–61 micron mesh; elution with methylene chloride/methanol/concentrated aqueous ammonium hydroxide=90:9:1 in volume) afforded the title compound (67 mg, 29.4% yield) as a viscous light yellow syrup.

MS m/z 225 (M+1).

$^1$H NMR (400 MHz, CDCl$_3$) δ 8.79 (1H, m), 7.88 (1H, m), 7.66 (1H, M), 7.53 (1H, m), 7.44 (1H, m), 6.85 (1H, M0, 4.46 (1H, m), 4.10 (1H, m), 2.82 (2H, q, J=7.5 Hz), 1.33 (3H, t, J=7.5 Hz) ppm.

The entire 67 mg sample was converted to the mono-hydrochloride salt by dissolution in 3 ml of ethyl acetate, followed by addition of 0.5 ml of saturated hydrochloric acid in ethyl acetate. The hydrochloride salt immediately precipitated as a pale yellow amorphous solid, which was isolated in quantitative yield by removal of solvent and excess hydrochloric acid in vacuo. The hydrochloride salt was utilized in the next preparative procedure (Step 3).

Step 3

Racemic 3-Ethyl-8-pyrrolidin-3-yl-quinoline (Semi-Purified; Purification: Steps 4/5 Below)

The title compound from the previous step (in hydrochloride salt form, 75 mg, 0.29 mmol) was dissolved in methanol (5.0 ml), and hydrogenated (50 psi, 10 mg of platinum oxide catalyst). The catalyst was filtered and the filtrate was concentrated in vacuo yielding a light amber residue. The residue was dissolved in 5 ml of water. The solution was extracted with 10 ml of ethyl acetate, the organic extract then being discarded. The aqueous solution was made basic (pH 14) by addition of 50% aqueous sodium hydroxide, and then extracted twice with 10 ml portions of methylene chloride. The combined methylene chloride extracts were, in turn, extracted with an equal volume portion of brine, dried (anhydrous sodium sulfate), and finally concentrated in vacuo to afford a colorless syrup. Flash chromatography of the entire sample (silica gel, 47–61 micron mesh; elution with methylene chloride/methanol/aqueous concentrated ammonium hydroxide=90:9:1 in volume) afforded the title compound (30 mg, 46.1% yield) as a pale yellow amorphous foam.

Final Purification of the Title Compound Product

Final purification of the just described 30 mg sample of title compound was accomplished by tert-butyloxycarbonyl acylation at the pyrrolidine nitrogen (to facilitate a further chromatographic purification) followed by acid catalyzed removal of the tert-butyloxycarbonyl substituent. This procedure afforded the final purified title compound (after basic work-up) in the free base form.

Step 4

Racemic 3-(3-Ethyl-quinolin-8-yl)-pyrrolidine-1-carboxylic Acid Tert-Butyl Ester To a well-stirred solution of the 15 mg (0.07 mmol) sample of semi-purified title compound product from the previous step and triethylamine (0.02 ml, 0.14 mmol) in methylene chloride, di-tert-butyl carbonate (21.8 mg, 0.10 mmol) was added. The reaction was then stirred at ambient temperature for 48 hours. Aqueous saturated sodium bicarbonate (5 ml) was added with efficient stirring. The mixture was then extracted with two 3 ml portions of methylene chloride. The organic extracts were combined and, in turn, extracted with an equal volume of brine, dried (anhydrous sodium sulfate). Concentration in vacuo afforded a viscous syrup. Flash chromatography of the entire sample (silica gel, 47–61 micron mesh; initially eluting with methylene chloride/methanol=99.75:0.25 in volume) steadily increasing the polarity of the eluting system finally to methylene chloride/methanol=99:1 in volume) afforded the title compound (15 mg, 69.7% yield) as a colorless oil.

MS m/z 327 (M+1).

$^1$H NMR (400 MHz, CDCl$_3$) δ 8.78 (1H, m), 7.88 (1H, m), 7.63 (1H, m), 7.40–7.54 (2H, overlapping multiplets), 4.63 (1H, m), 3.96 (1H, m), 3.50 (2H, m), 3.33 (1H, m), 2.82 (2H, q, J=7.5 Hz), 2.34 (1H, m), 2.12 (1H, m), 1.44 and 1.47 (9H, two singlets), 1.33 (3H, t, J=7.5 Hz) ppm.

Step 5

Racemic 3-Ethyl-8-pyrrolidin-3-yl-quinoline

To a solution of 15 mg (0.05 mmol) of the title compound from the previous step in methylene chloride/methanol=9:2 in volume, a 1.0 ml saturated anhydrous hydrogen chloride/diethyl ether solution was added, and the resulting reaction mixture was stirred at ambient temperature for 18 hours. Solvents were removed in vacuo, and the residue was extracted into water. The aqueous extract was, in turn, extracted with an equal volume of ethyl acetate. Finally, the separated aqueous phase was made basic (pH=14) by addition of 50% aqueous sodium hydroxide, and then extracted with three 5 ml portions of ethyl acetate. The combined organic extracts were dried (anhydrous sodium sulfate) and concentrated in vacuo to afford the purified title compound (free base form, 10 mg, 96% yield) as a colorless amorphous solid.

MS m/z 227 (M+1).

$^1$H NMR (400 MHz, CDCl$_3$) δ8.76 (1H, m), 7.89 (1H, m), 7.60 (1H, m), 7.53 (1H, m), 7.44 (1H, m), 4.38 (1H, m), 3.46 (1H, m), 3.27 (1H, m), 3.12 (1H, m), 2.97 (1H, m), 2.82 (2H, q, J=7.5 Hz), 2.32 (1H, m), 2.01 (1H, m), 1.33 (3H, t, J=7.5 Hz) ppm.

Step 6

Enantiomeric (Both Enantiomers) 3-Ethyl-8-pyridin-3-yl-quinoline

Utilizing analogously the procedure of Step 4/Example 1, the racemic title compound of the previous step of this example was converted to the corresponding racemic nitrogen substituted tert-butoxycarbonyl compound, the separated/purified enantiomers of which were then isolated by the methodology of Step 6/Example 1. Finally, by the procedure of Step 6/Example 1, the enantiomers of the title compound of the previous step of this example were prepared in both mono-hydrochloride and free base form.

Example 10

Enantiomeric (Both Enantiomers) and Racemic 3-Ethyl-7-Piperidin-3-yl-Quinoline

Step 1

7-Bromo-3-ethyl-quinoline

To a well-stirred mixture consisting of 3-bromo-aniline (5.40 g, 31.4 mmol), sodium 3-nitro-benzene sulfonate (4.25 g, 18.9 mmol), 8.5 g (177 mmol) of concentrated sulfuric acid, and 3.2 ml of water heated to 100° C., 2-ethyl acrolein (5.0 ml, 51 mmol) was added. After maintaining the reaction temperature at 100° C. for 1 hour, the temperature was elevated to 110° C. An additional portion of 2-ethyl acrolein (1.0 ml, 10.2 mmol) was added, and the reaction was stirred at 110° C. for 1 hour. The reaction temperature was then elevated to 120° C. prior to addition of another 1.0 ml (10.2 mmol) portion of 2-ethyl acrolein. After heating the reaction at 120° C. for 1 hour, the temperature was increased to 130° C. prior to addition of 1.0 ml (10.2 mmol) of 2-ethyl acrolein. Finally, the reaction temperature was raised to 140° C. and maintained at that temperature for 2 hours after addition of a final portion (1.3 ml, 13.2 mol) of 2-ethyl acrolein. The cooled reaction was quenched with ice (50 g), and the pH of the resulting mixture was adjusted to by addition of 6 N aqueous sodium hydroxide. The mixture was then extracted with two 30 ml portions of methylene chloride. The combined organic extracts were dried (anhydrous sodium sulfate) and concentrated in vacuo, affording an amber oil. Flash chromatography of the entire sample utilizing the Biotage Flash 401i™ silica gel flash chromatography module and manufacturer's prepacked silica gel cartridges described in Example 1, Step 4, and eluting with methylene chloride, afforded the title compound (1.46 g, 19.7% yield) as a viscous light amber syrup which solid on standing.

MS m/z 236, 237, 238, 239 (M+1).

$^1$H NMR (400 MHz, CDCl$_3$) δ 8.77 (1H, m), 8.23 (1H, m), 7.87 (1H, m), 7.54–7.63 (2H, overlapping multiplets), 2.80 (2H, q, J=7.5 Hz), 1.33 (3H, t, J=7.5 Hz) ppm.

Step 2

3-Ethyl-7-pyridin-3-yl-quinoline

To a well-stirred mixture consisting of the title compound of Step 1, this Example (1.40 g, 5.93 mmol), diethyl(3-pyridyl)borane (0.96 g, 6.53 mmol) and bis(triphenylphosphine) palladium (II) chloride (458 mg, 0.65 mmol) in tetrahydrofuran (15 ml), a 7.5 ml aqueous solution of sodium carbonate (2.51 g, 23.7 mmol) was added. The reaction mixture was then stirred at 90° C. for 5 hours, and then at ambient temperature for 18 hours. The aqueous phase of the biphasic reaction mixture is separated and extracted with an equal volume of ethyl acetate. The solvent of the organic phase of the reaction mixture was removed in vacuo and the residue is extracted with ethyl acetate (25 ml). The combined organic extracts are dried (anhydrous sodium sulfate) and concentrated in vacuo, yielding a dark viscous oil. Flash chromatography of the entire sample (silica gel, 47–61 micron mesh; elution with ethyl acetate) afford the title compound (807 mg, 58% yield) as a viscous yellow syrup.

$^1$H NMR (400 MHz, CDCl$_3$) δ 8.93 (1H, m), 8.82 (1H, m), 8.62 (1H, m), 8.27 (1H, m), 8.01 (1H, m), 7.94 (1H, m), 7.86 (1H, m). 7.74 (1H, m), 7.36–7.49 (2H, overlapping multiplets), 2.84 (2H, q, J=7.5 Hz), 1.35 (3H, t, J=7.5 Hz) ppm.

Step 3

Racemic 3-Ethyl-7-piperidin-3-yl-quinoline

To a well-stirred solution of the title compound of the previous step (780 mg, 3.33 mmol) in anhydrous tetrahydrofuran (8 ml), 27.0 ml of a 1 M solution of lithium triethyl borohydride (27 mmol) in tetrahydrofuran was added, and the resulting reaction mixture was stirred at ambient temperature for 18 hours. The reaction was quenched by cautious dropwise addition of water (50 ml). Solvents were removed in vacuo, affording a viscous oil which was extracted with three 20 ml portions of methylene chloride. The combined organic extracts dried (anhydrous sodium sulfate) and concentrated in vacuo, yielding a viscous syrup. Flash chromatography of the entire sample (silica gel, 47–61 micron mesh; elution with methylene chloride/methanol/concentrated aqueous ammonium hydroxide=90:9:1 in volume) afford the title compound (390 mg, 48.8% yield) as a yellow gum.

MS m/z 241 (M+1).

$^1$H NMR (400 MHz, CDCl$_3$) δ 8.73 (1H, m), 7.86 (2H, overlapping multiplets), 7.66 (1H, m), 7.37 (1H, m), 3.27 (1H, m), 3.15 (1H, m), 2.88 (1H, m), 2.7–2.9 (2H, overlapping multiplets), 2.66 (1H, m), 2.78 (2H, q, J=7.5 Hz), 1.83 (1H, m), 1.60–1.82 (2H, overlapping multiplets), 1.31 (3H, t, J=7.5 Hz) ppm.

Separation of the Enantiomers of the Racemic Title Compound

Step 4

Racemic 3-(3-Ethyl-quinolin-7-yl)-piperidine-1-carboxylic Acid Tert-Butyl Ester

A reaction mixture consisting of the free base title compound from the previous step (390 mg, 1.63 mmol), triethylamine (0.45 ml, 3.25 mmol), and di-tert-butyl dicarbonate (530 mg, 2.44 mmol) in methylene chloride (15 ml) was stirred at ambient temperature for 18 hours. Saturated aqueous sodium bicarbonate (20 ml) was added with efficient stirring. The mixture was then extracted with two 10 ml portions of methylene chloride. The combing organic extracts were, in turn, extracted with an equal volume portion of brine, dried (anhydrous sodium sulfate), and concentrated in vacuo, yielding a viscous syrup. Flash chromatography of the entire sample (silica gel, 47–61 micron mesh; elution with hexanes/ethyl acetate=75:25 in volume) afforded the title compound (180 mg, 32% yield) as a colorless oil.

MS m/z 341 (M+1).

Step 5

Enantiomeric 3-(3-Ethyl-quinolin-7-yl)-piperidine-1-carboxylic Acid Tert-Butyl Ester (Both Enantiomers)

Utilizing the method of Example 1, Step 5, the enantiomers of the racemic title compound of Step 4 of this Example were separated.

Step 6

Enantiomeric 3-Ethyl-7-piperidin-3-yl-quinoline (Both Enantiomers)

Utilizing the method of Example 1, Step 6, the enantiomers of the previous Step of this Example were used to prepare the title compound enantiomers of this step in both mono-hydrochloride and free base forms.

Example 11

Enantiomeric (Both Enantiomers) and Racemic 3-Methyl-8-(1-Methyl-Piperidin-3-yl)Quinoline Step 1

Racemic 3-Methyl-8-(1-methyl-piperidin-3-yl)quinoline

To a well-stirred solution of the title compound of Example 8, Step 2 (30 mg, 0.133 mmol) in 1.0 ml of methanol, 0.10 ml of 37% formaldehyde in methanol (1.2 mmol of formaldehyde) and 100 mg (0.47 mmol) of sodium triacetoxyborohydride were sequentially added, and the resulting reaction mixture was stirred at ambient temperature for 6 hours. The solvent was removed in vacuo, and the resulting residue was extracted into 10 ml of methylene chloride. The organic extract was, in turn, extracted with an equal volume portion of aqueous saturated sodium bicarbonate, and then with an equal volume portion of brine. After drying (anhydrous magnesium sulfate), the methylene chloride was removed in vacuo, yielding a light amber solid (40 mg). Flash chromatography of the entire sample (silica gel. 47–61 micron mesh; elution with methylene chloride/methanol/concentrated aqueous ammonium hydroxide=90:9:1 in volume) afforded the title compound (19 mg, 60% yield) as a colorless amorphous solid.

MS m/z 241 (M+).

$^1$H NMR (400 MHz, CDCl$_3$) δ 8.76 (1H, m), 7.86 (1H, m), 7.56 (1H, m), 7.48 (1H, m), 7.43 (1H, m), 4.29 (1H, m), 3.12 (1H, m), 2.97 (1H, m), 2.49 (3H, s), 2.33 (3H, s), 1.80–2.13 (5H, overlapping multiplets), 1.64 (1H, m) ppm.

Step 2

Enantiomeric (Both Enantiomers)3-Methyl-8-(1-methyl-piperidin-3-yl)quinoline

Utilizing the general methodology for enantiomer separation described in Step 5/Example 1, the enantiomers of the racemic title compound of the previous step were isolated in free base form. The mono-hydrochloride salts of the enantiomers were prepared by the procedure of Step 2/Example 9.

What is claimed is:

1. A quinoline compound with a non-quinoline ring attached thereto of the Formula

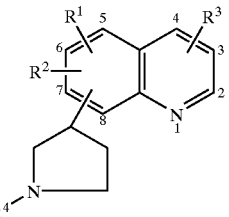

or pharmaceutically acceptable salts thereof;
wherein $R^1$, $R^2$ and $R^3$ are independently selected from the group consisting of hydrogen, halo, $(C_1-C_6)$alkyl optionally substituted with from one to three halo atoms and (C$_1$–C$_6$)alkoxy optionally substituted with from one to three halo atoms; and R$^4$ is hydrogen or (C$_1$–C$_3$).

2. A compound according to claim 1, wherein either R$^1$ and R$^2$ are both hydrogen or one of R$^1$ and R$^2$ is hydrogen and the other is attached at position 5.

3. A compound according to claim 1 wherein either R$^1$ and R$^2$ are both hydrogen or one of R$^1$ and R$^2$ is hydrogen and the other is attached at position 5, and the non-quinoline ring is attached at position 7.

4. A compound selected from the group consisting of:
R and S-(3-Ethyl-7-methyl-8-piperidin-3-yl-quinoline);
R, S-(3-Ethyl-7-methyl-8-piperidin-3-yl-quinoline);
R and S-(3,6-Dimethyl-8-piperidin-3-yl-quinoline);
R, S-(3,6-Dimethyl-8-piperidin-3-yl-quinoline);
R and S-(3,7-Dimethyl-8-piperidin-3-yl-quinoline);
R, S-(3,7-Dimethyl-8-piperidin-3-yl-quinoline);
R and S-(3,5-Dimethyl-8-piperidin-3-yl-quinoline);
R,S-(3,5-Dimethyl-8-piperidin-3-yl-quinoline);
R and S-(6-Chloro-3-methyl-8-piperidin-3-yl-quinoline);
R, S-(6-Chloro-3-methyl-8-piperidin-3-yl-quinoline);
R and S-(4-Methyl-8-piperidin-3-yl-quinoline);
R, S-(4-Methyl-8-piperidin-3-yl-quinoline);
R and S-(3-Methyl-8-piperidin-3-yl-quinoline);
R, S-(3-Methyl-8-piperidin-3-yl-quinoline);
R and S-(3-Ethyl-8-piperidin-3-yl-quinoline);
R, S-(3-Ethyl-8-piperidin-3-yl-quinoline);
R and S-(Ethyl-7-piperidin-3-yl-quinoline);
R, S-(Ethyl-7-piperidin-3-yl-quinoline);
R and S-[3-Methyl-8-(1-methyl-piperidin-3-yl)-quinoline];
R, S-[3-Methyl-8-(1-methyl-piperidin-3-yl)-quinoline];
3-Ethyl-7-methyl-8-(1-methyl-piperidin-3-yl)-quinoline;
3-Ethyl-8-methyl-8-(1-ethyl-piperidin-3-yl)-7-methyl-quinoline;
3,6-Dimethyl-8-(1-methyl-piperidin-3-yl)-quinoline;
8-(1-Ethyl-piperidin-3-yl)-3,6-dimethyl-quinoline;
3,7-Dimethyl-8-(1-methyl-piperidin-3-yl)-quinoline;
8-(1-Ethyl-piperidin-3-yl)-3,7-dimethyl-quinoline;
3,5-Dimethyl-8-(1-methyl-piperidin-3-yl)-quinoline;
8-(1-Ethyl-7-piperidin-3-yl)-3,5-dimethyl-quinoline;
6-Chloro-3-methyl-8-(1-methyl-piperidin-3-yl)-quinoline;
6-Chloro-8-(1-ethyl-piperidin-3-yl)-3-methyl-quinoline;
3-Ethyl-8-(1-methyl-piperidin-3-yl)-quinoline;
3-Ethyl-8-(1-ethyl-piperidin-3-yl)-quinoline;
4-Methyl-8-(1-methyl-piperidin-3-yl)-quinoline;
8-(1-Ethyl-piperidin-3-yl)-4-methyl-quinoline;
3-Methyl-8-(1-methyl-piperidin-3-yl)-quinoline;
8-(1-Ethyl-piperidin-3-yl)-3-methyl-quinoline;
3-Ethyl-8-(1-methyl-pyrrolidin-3-yl)-quinoline;
3-Ethyl-8-(1-ethyl-pyrrolidin-3-yl)-quinoline;
3-Ethyl-7-(1-methyl-piperidin-3-yl)-quinoline;
3-Ethyl-7-(1-ethyl-piperidin-3-yl)-quinoline;
3-Ethyl-7-pyrrolidin-3-yl)-quinoline;
3-Ethyl-7-(1-methyl-pyrrolidin-3-yl)-quinoline;
3-Ethyl-7-(1-ethyl-pyrrolidin-3-yl)-quinoline;
3-Ethyl-7-pyrrolidin-3-yl)-quinoline;
3-Ethyl-7-(1-methyl-pyrrolidin-3-yl)-quinoline;
3-Ethyl-7-(1-ethyl-pyrrolidin-3-yl)-quinoline; and
pharmaceutically acceptable salts thereof.

5. A compound according to claim 1,
wherein R$^1$ and R$^3$ are independently hydrogen, halo, (C$_1$–C$_6$)alkyl optionally substituted with from one to three halo atoms or (C$_1$–C$_6$)alkoxy optionally substituted with from one to three halo atoms; and R$^4$ is hydrogen or (C$_1$–C$_3$)alkyl.

6. A pharmaceutical composition comprising a therapeutically effective amount of a compound according to claim 1, or a pharmaceutically acceptable salt thereof, and a pharmaceutically acceptable carrier.

7. A quinoline compound with a non-quinoline ring attached, having the formula:

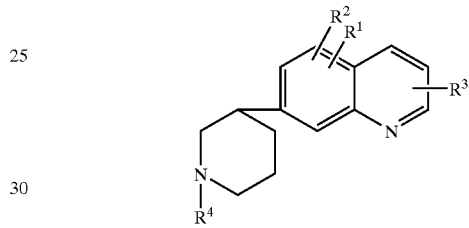

or pharmaceutically acceptable salts thereof;
wherein R$^1$ and R$^3$ are independently selected from hydrogen, halo, (C$_1$–C$_6$)alkyl optionally substituted with from one to three halo atoms; and (C$_1$–C$_6$)alkoxy substituted with from one to three halo atoms; and R$^4$ is hydrogen or (C$_1$–C$_3$)alkyl.

8. A compound according to claim 7 wherein either R$^1$ and R$^2$ is hydrogen and the other is attached at position 5.

9. A compound according to claim 7 wherein either R$^1$ and R$^2$ are both hydrogen, one of R$^1$ and R$^2$ is hydrogen and the other is attached at position 5, and the non-quinoline ring is attached at position 7.

10. A pharmaceutical composition comprising a therapeutically effective amount of a compound according to claim 7 or a pharmaceutically salt thereof and a pharmaceutically acceptable carrier.

* * * * *